(12) United States Patent
Bumbalough

(10) Patent No.: US 9,968,441 B2
(45) Date of Patent: May 15, 2018

(54) INTRAOCULAR LENS HAVING A HAPTIC THAT INCLUDES A CAP

(75) Inventor: Timothy R. Bumbalough, Fullerton, CA (US)

(73) Assignee: Johnson & Johnson Surgical Vision, Inc., Santa Ana, CA (US)

(*) Notice: Subject to any disclaimer, the term of this patent is extended or adjusted under 35 U.S.C. 154(b) by 104 days.

(21) Appl. No.: 13/243,366

(22) Filed: Sep. 23, 2011

(65) Prior Publication Data

US 2012/0143327 A1    Jun. 7, 2012

Related U.S. Application Data

(63) Continuation of application No. 12/057,633, filed on Mar. 28, 2008, now Pat. No. 8,034,108.

(51) Int. Cl.
*A61F 2/16* (2006.01)

(52) U.S. Cl.
CPC .......... *A61F 2/1635* (2013.01); *A61F 2/1624* (2013.01)

(58) Field of Classification Search
CPC .... A61F 2/1613; A61F 2/1635; A61F 2/1648; A61F 2/16; A61F 2250/0053; A61F 2/1629; A61F 2009/00872; A61F 2002/1681; A61F 2/1624; A61F 2/1694; A61F 9/00808; A61F 2009/00844; A61F 2009/00853; A61F 2009/00895; A61F 2220/0016; A61F 2240/001; A61F 2250/0029; A61F 2250/0069; A61F 2/145; A61F 2/1451; A61F 2/147; A61F 2/1601; A61F 2/1627; A61F 2/1651;

(Continued)

(56) References Cited

U.S. PATENT DOCUMENTS

| 1,483,509 A | 5/1921 | Bugbee |
| 2,129,305 A | 9/1938 | Feinbloom |
| 2,274,142 A | 2/1942 | Houchin |

(Continued)

FOREIGN PATENT DOCUMENTS

| AU | 3225789 A1 | 10/1989 |
| CA | 2752743 A1 | 9/2010 |

(Continued)

OTHER PUBLICATIONS

Amo Specs Model AC-21B, 1992.

(Continued)

*Primary Examiner* — Thomas J Sweet
*Assistant Examiner* — Seema Mathew
(74) *Attorney, Agent, or Firm* — Johnson & Johnson Surgical Vision, Inc.

(57) ABSTRACT

A deformable intraocular has a haptic that supports the optic around its equator and couples the optic to the capsular bag of the eye. The haptic may include a cap on one or both surfaces of the lens. The lens may include a force transfer member that couples forces from the haptic to the cap, so that a radial force on the haptic changes the curvature of the cap. The cap may be made of the haptic material, which is stiffer than the optic material, and can influence the deformation of the lens during accommodation. A cap on the anterior surface may produce an axial movement of the lens in an anterior direction during accommodation. The cap may also protect the surfaces of the optic during handling and installation.

11 Claims, 19 Drawing Sheets

(58) Field of Classification Search
CPC ........ A61F 2/1616; A61F 2/14; A61F 2/1618; A61F 2/164; A61F 9/0017
USPC ..................................................... 623/6.37
See application file for complete search history.

(56) References Cited

U.S. PATENT DOCUMENTS

| | | |
|---|---|---|
| 2,405,989 A | 8/1946 | Beach |
| 2,511,517 A | 6/1950 | Spiegel |
| 2,834,023 A | 5/1958 | Lieb |
| 3,004,470 A | 10/1961 | Hans |
| 3,031,927 A | 5/1962 | Wesley |
| 3,034,403 A | 5/1962 | Neefe |
| RE25,286 E | 11/1962 | DeCarle |
| 3,210,894 A | 10/1965 | Bentley et al. |
| 3,222,432 A | 12/1965 | Grandperret |
| 3,227,507 A | 1/1966 | Feinbloom |
| 3,305,294 A | 2/1967 | Alvarez |
| 3,339,997 A | 9/1967 | Wesley |
| 3,415,597 A | 12/1968 | Willard |
| 3,420,006 A | 1/1969 | Barnett |
| 3,431,327 A | 3/1969 | Tsuetaki |
| 3,482,906 A | 12/1969 | Volk |
| 3,507,565 A | 4/1970 | Luis |
| 3,542,461 A | 11/1970 | Girard et al. |
| 3,583,790 A | 6/1971 | Baker |
| 3,617,116 A | 11/1971 | Jones |
| 3,632,696 A | 1/1972 | Donald |
| 3,673,616 A | 7/1972 | Fedorov et al. |
| 3,673,816 A | 7/1972 | Kuszaj |
| 3,693,301 A | 9/1972 | Lemaitre |
| 3,711,870 A | 1/1973 | Deitrick |
| 3,718,870 A | 2/1973 | Keller |
| 3,751,138 A | 8/1973 | Humphrey |
| 3,760,045 A | 9/1973 | Thiele et al. |
| 3,794,414 A | 2/1974 | Wesley |
| 3,827,798 A | 8/1974 | Alvarez |
| 3,866,249 A | 2/1975 | Flom |
| 3,906,551 A | 9/1975 | Otter |
| 3,913,148 A | 10/1975 | Potthast |
| 3,922,728 A | 12/1975 | Krasnov |
| 3,925,825 A | 12/1975 | Richards et al. |
| 3,932,148 A | 1/1976 | Krewalk, Sr. |
| 3,996,626 A | 12/1976 | Richards et al. |
| 4,010,496 A | 3/1977 | Neefe |
| 4,014,049 A | 3/1977 | Richards et al. |
| 4,038,088 A | 7/1977 | White et al. |
| 4,041,552 A | 8/1977 | Ganias |
| 4,053,953 A | 10/1977 | Flom et al. |
| 4,055,378 A | 10/1977 | Feneberg et al. |
| 4,056,855 A | 11/1977 | Kelman |
| 4,062,629 A | 12/1977 | Winthrop |
| 4,073,579 A | 2/1978 | Deeg et al. |
| 4,074,368 A | 2/1978 | Levy, Jr. et al. |
| 4,087,866 A | 5/1978 | Choyce et al. |
| 4,102,567 A | 7/1978 | Cuffe et al. |
| 4,110,848 A | 9/1978 | Jensen |
| 4,118,808 A | 10/1978 | Poler |
| 4,159,546 A | 7/1979 | Shearing |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,163 A | 12/1980 | Galin |
| 4,240,719 A | 12/1980 | Guilino et al. |
| 4,244,060 A | 1/1981 | Hoffer |
| 4,244,597 A | 1/1981 | Dandl |
| 4,251,887 A | 2/1981 | Anis |
| 4,253,199 A | 3/1981 | Banko |
| 4,254,509 A | 3/1981 | Tennant |
| 4,261,065 A | 4/1981 | Tennant |
| 4,274,717 A | 6/1981 | Davenport |
| 4,285,072 A | 8/1981 | Morcher et al. |
| 4,298,994 A | 11/1981 | Clayman |
| 4,304,012 A | 12/1981 | Richard |
| 4,307,945 A | 12/1981 | Kitchen et al. |
| 4,315,336 A | 2/1982 | Poler |
| 4,315,673 A | 2/1982 | Guilino et al. |
| 4,316,293 A | 2/1982 | Bayers |
| 4,326,306 A * | 4/1982 | Poler .......................... A61F 2/16 206/205 |
| 4,338,005 A | 7/1982 | Cohen |
| 4,340,283 A | 7/1982 | Cohen |
| 4,340,979 A | 7/1982 | Kelman |
| 4,361,913 A | 12/1982 | Streck |
| 4,363,143 A | 12/1982 | Callahan |
| 4,366,582 A | 1/1983 | Faulkner |
| 4,370,760 A | 2/1983 | Kelman |
| 4,373,218 A | 2/1983 | Schachar |
| 4,377,329 A | 3/1983 | Poler |
| 4,377,873 A | 3/1983 | Reichert, Jr. |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,424,597 A | 1/1984 | Schlegel |
| 4,426,741 A | 1/1984 | Bittner |
| 4,435,856 A | 3/1984 | L'Esperance |
| 4,442,553 A | 4/1984 | Hessburg |
| 4,457,592 A | 7/1984 | Baker |
| 4,463,458 A | 8/1984 | Seidner |
| 4,474,751 A | 10/1984 | Haslam et al. |
| 4,474,752 A | 10/1984 | Haslam et al. |
| 4,474,753 A | 10/1984 | Haslam et al. |
| 4,476,591 A | 10/1984 | Arnott |
| 4,478,822 A | 10/1984 | Haslam et al. |
| 4,503,953 A | 3/1985 | Majewski |
| 4,504,981 A | 3/1985 | Walman |
| 4,504,982 A | 3/1985 | Burk |
| 4,512,040 A | 4/1985 | McClure |
| 4,542,542 A | 9/1985 | Wright |
| 4,551,864 A | 11/1985 | Akhavi |
| 4,560,383 A | 12/1985 | Leiske |
| 4,562,600 A | 1/1986 | Ginsberg et al. |
| 4,573,775 A | 3/1986 | Bayshore |
| 4,573,998 A | 3/1986 | Mazzocco |
| 4,575,877 A | 3/1986 | Herrick |
| 4,575,878 A | 3/1986 | Dubroff |
| 4,576,607 A | 3/1986 | Kelman |
| 4,580,882 A | 4/1986 | Nuchman et al. |
| 4,581,033 A | 4/1986 | Callahan |
| 4,596,578 A | 6/1986 | Kelman |
| 4,601,545 A | 7/1986 | Kern |
| 4,608,050 A | 8/1986 | Wright et al. |
| 4,615,701 A | 10/1986 | Woods |
| 4,617,023 A | 10/1986 | Peyman |
| 4,618,228 A | 10/1986 | Baron et al. |
| 4,618,229 A | 10/1986 | Jacobstein et al. |
| 4,624,669 A | 11/1986 | Grendahl |
| 4,629,460 A | 12/1986 | Dyer |
| 4,636,049 A | 1/1987 | Blaker |
| 4,636,210 A | 1/1987 | Hoffer |
| 4,636,211 A | 1/1987 | Nielsen et al. |
| 4,637,697 A | 1/1987 | Freeman |
| 4,641,934 A | 2/1987 | Freeman |
| 4,642,112 A | 2/1987 | Freeman |
| 4,642,114 A | 2/1987 | Rosa |
| 4,646,720 A | 3/1987 | Peyman et al. |
| 4,648,878 A | 3/1987 | Kelman |
| 4,650,292 A | 3/1987 | Baker et al. |
| 4,655,770 A | 4/1987 | Gupta et al. |
| 4,661,108 A | 4/1987 | Grendahl et al. |
| 4,662,882 A | 5/1987 | Hoffer |
| 4,664,666 A | 5/1987 | Barrett |
| 4,666,444 A | 5/1987 | Pannu |
| 4,666,445 A | 5/1987 | Tillay |
| 4,676,792 A | 6/1987 | Praeger |
| 4,676,793 A | 6/1987 | Bechert, II |
| 4,687,484 A | 8/1987 | Kaplan |
| 4,693,572 A | 9/1987 | Tsuetaki et al. |
| 4,693,716 A | 9/1987 | MacKool |
| RE32,525 E | 10/1987 | Pannu |
| 4,702,244 A | 10/1987 | Mazzocco |
| 4,704,016 A | 11/1987 | De Carle |

(56) References Cited

U.S. PATENT DOCUMENTS

| | | |
|---|---|---|
| 4,710,193 A | 12/1987 | Volk |
| 4,710,194 A | 12/1987 | Kelman |
| 4,711,638 A | 12/1987 | Lindstrom |
| 4,720,286 A | 1/1988 | Bailey et al. |
| 4,725,278 A | 2/1988 | Shearing |
| 4,731,078 A | 3/1988 | Stoy et al. |
| 4,737,322 A | 4/1988 | Bruns et al. |
| 4,752,123 A | 6/1988 | Blaker |
| 4,759,762 A | 7/1988 | Grendahl |
| 4,769,033 A | 9/1988 | Nordan |
| 4,769,035 A | 9/1988 | Kelman |
| 4,780,154 A | 10/1988 | Mori et al. |
| 4,781,718 A | 11/1988 | Lindstrom |
| 4,787,903 A | 11/1988 | Grendahl |
| 4,790,847 A | 12/1988 | Woods |
| 4,808,170 A | 2/1989 | Thornton et al. |
| 4,813,955 A | 3/1989 | Achatz et al. |
| 4,816,030 A | 3/1989 | Robinson |
| 4,816,031 A | 3/1989 | Pfoff |
| 4,816,032 A | 3/1989 | Hetland |
| 4,822,360 A | 4/1989 | Deacon |
| 4,828,558 A | 5/1989 | Kelman |
| 4,830,481 A | 5/1989 | Futhey et al. |
| 4,834,749 A | 5/1989 | Orlosky |
| 4,840,627 A | 6/1989 | Blumenthal |
| 4,842,601 A | 6/1989 | Smith |
| 4,865,601 A | 9/1989 | Caldwell et al. |
| 4,878,910 A | 11/1989 | Koziol et al. |
| 4,878,911 A | 11/1989 | Anis |
| 4,880,427 A | 11/1989 | Anis |
| 4,881,804 A | 11/1989 | Cohen |
| 4,883,485 A | 11/1989 | Patel |
| 4,888,012 A | 12/1989 | Horn et al. |
| 4,888,014 A | 12/1989 | Nguyen |
| 4,888,015 A | 12/1989 | Domino |
| 4,888,016 A | 12/1989 | Langerman |
| 4,890,912 A | 1/1990 | Visser |
| 4,890,913 A | 1/1990 | De Carle |
| 4,892,543 A | 1/1990 | Turley |
| 4,898,416 A | 2/1990 | Hubbard et al. |
| 4,898,461 A | 2/1990 | Portney |
| 4,902,293 A | 2/1990 | Feaster |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,929,289 A | 5/1990 | Moriya et al. |
| 4,932,966 A | 6/1990 | Christie et al. |
| 4,932,968 A | 6/1990 | Caldwell et al. |
| 4,932,971 A | 6/1990 | Kelman |
| 4,938,583 A | 7/1990 | Miller |
| 4,946,469 A | 8/1990 | Sarfarazi |
| 4,955,902 A | 9/1990 | Kelman |
| 4,961,746 A | 10/1990 | Lim et al. |
| 4,963,148 A | 10/1990 | Sulc et al. |
| 4,976,534 A | 12/1990 | Miege et al. |
| 4,976,732 A | 12/1990 | Vorosmarthy |
| 4,990,159 A | 2/1991 | Kraff |
| 4,994,058 A | 2/1991 | Raven et al. |
| 4,994,080 A | 2/1991 | Shepard |
| 4,994,082 A | 2/1991 | Richards et al. |
| 4,994,083 A | 2/1991 | Sulc et al. |
| 4,995,880 A | 2/1991 | Galib |
| 4,997,442 A | 3/1991 | Barrett |
| 5,000,559 A | 3/1991 | Takahashi et al. |
| 5,002,382 A | 3/1991 | Seidner |
| 5,002,571 A | 3/1991 | O'Donnell et al. |
| 5,018,504 A | 5/1991 | Terbrugge et al. |
| 5,019,098 A | 5/1991 | Mercier |
| 5,019,099 A | 5/1991 | Nordan |
| 5,026,396 A | 6/1991 | Darin |
| 5,044,742 A | 9/1991 | Cohen |
| 5,047,051 A | 9/1991 | Cumming |
| 5,047,052 A | 9/1991 | Dubroff |
| 5,054,905 A | 10/1991 | Cohen |
| 5,056,908 A | 10/1991 | Cohen |
| 5,066,301 A | 11/1991 | Wiley |
| 5,071,432 A | 12/1991 | Baikoff |
| 5,074,877 A | 12/1991 | Nordan |
| 5,074,942 A | 12/1991 | Kearns et al. |
| 5,078,740 A | 1/1992 | Walman |
| 5,089,024 A | 2/1992 | Christie et al. |
| 5,096,285 A | 3/1992 | Silberman |
| 5,108,429 A | 4/1992 | Wiley |
| 5,112,351 A | 5/1992 | Christie et al. |
| 5,117,306 A | 5/1992 | Cohen |
| 5,123,921 A | 6/1992 | Werblin et al. |
| 5,129,718 A | 7/1992 | Futhey et al. |
| 5,133,748 A | 7/1992 | Feaster |
| 5,133,749 A | 7/1992 | Nordan |
| 5,141,507 A | 8/1992 | Parekh |
| 5,147,397 A | 9/1992 | Christ et al. |
| 5,152,788 A | 10/1992 | Isaacson et al. |
| 5,152,789 A | 10/1992 | Willis |
| 5,158,572 A | 10/1992 | Nielsen |
| 5,166,711 A | 11/1992 | Portney |
| 5,166,712 A | 11/1992 | Portney |
| 5,166,719 A | 11/1992 | Chinzei et al. |
| 5,171,266 A | 12/1992 | Wiley et al. |
| 5,171,267 A | 12/1992 | Ratner et al. |
| 5,171,320 A | 12/1992 | Nishi |
| 5,172,723 A | 12/1992 | Sturgis |
| 5,173,723 A | 12/1992 | Volk |
| 5,180,390 A | 1/1993 | Drews |
| 5,192,317 A | 3/1993 | Kalb |
| 5,192,318 A | 3/1993 | Schneider et al. |
| 5,196,026 A | 3/1993 | Barrett et al. |
| 5,197,981 A | 3/1993 | Southard |
| 5,201,762 A | 4/1993 | Hauber |
| 5,203,788 A | 4/1993 | Wiley |
| 5,213,579 A | 5/1993 | Yamada et al. |
| 5,217,491 A | 6/1993 | Vanderbilt |
| 5,225,858 A | 7/1993 | Portney |
| 5,229,797 A | 7/1993 | Futhey et al. |
| 5,236,452 A | 8/1993 | Nordan |
| 5,236,970 A | 8/1993 | Christ et al. |
| 5,258,025 A | 11/1993 | Fedorov et al. |
| 5,260,727 A | 11/1993 | Oksman et al. |
| 5,270,744 A | 12/1993 | Portney |
| 5,275,623 A | 1/1994 | Sarfarazi |
| 5,275,624 A | 1/1994 | Hara et al. |
| 5,296,881 A | 3/1994 | Freeman |
| 5,326,347 A | 7/1994 | Cumming |
| 5,336,261 A | 8/1994 | Barrett et al. |
| 5,344,448 A | 9/1994 | Schneider et al. |
| 5,349,394 A | 9/1994 | Freeman et al. |
| 5,354,335 A | 10/1994 | Lipshitz et al. |
| 5,358,520 A | 10/1994 | Patel |
| 5,366,499 A | 11/1994 | Py |
| 5,366,502 A | 11/1994 | Patel |
| 5,376,694 A | 12/1994 | Christ et al. |
| 5,391,202 A | 2/1995 | Lipshitz et al. |
| 5,405,386 A | 4/1995 | Rheinish et al. |
| 5,408,281 A | 4/1995 | Zhang |
| 5,423,929 A | 6/1995 | Doyle et al. |
| RE34,988 E | 7/1995 | Yang et al. |
| RE34,998 E | 7/1995 | Langerman |
| 5,443,506 A | 8/1995 | Garabet |
| 5,476,445 A | 12/1995 | Baerveldt et al. |
| 5,476,514 A | 12/1995 | Cumming |
| 5,480,428 A | 1/1996 | Fedorov et al. |
| 5,489,301 A | 2/1996 | Barber |
| 5,489,302 A | 2/1996 | Skottun |
| 5,494,946 A | 2/1996 | Christ et al. |
| 5,496,366 A | 3/1996 | Cumming |
| 5,503,165 A | 4/1996 | Schachar |
| 5,521,656 A | 5/1996 | Portney |
| 5,522,891 A | 6/1996 | Klaas |
| 5,523,029 A * | 6/1996 | Korgel ............... A61F 2/16 264/1.37 |
| 5,549,760 A | 8/1996 | Becker |
| 5,562,731 A | 10/1996 | Cumming |
| 5,574,518 A | 11/1996 | Mercure |

(56) References Cited

U.S. PATENT DOCUMENTS

| | | | |
|---|---|---|---|
| 5,578,081 A | 11/1996 | McDonald | |
| 5,593,436 A | 1/1997 | Langerman | |
| 5,607,472 A | 3/1997 | Thompson | |
| 5,608,471 A | 3/1997 | Miller | |
| 5,609,630 A | 3/1997 | Crozafon | |
| 5,628,795 A | 5/1997 | Langerman | |
| 5,628,796 A | 5/1997 | Suzuki | |
| 5,628,797 A | 5/1997 | Richer | |
| 5,650,837 A | 7/1997 | Roffman et al. | |
| 5,652,014 A | 7/1997 | Galin et al. | |
| 5,652,638 A | 7/1997 | Roffman et al. | |
| 5,653,754 A | 8/1997 | Nakajima et al. | |
| 5,657,108 A | 8/1997 | Portney | |
| 5,661,195 A | 8/1997 | Christ et al. | |
| 5,674,282 A | 10/1997 | Cumming | |
| 5,682,223 A | 10/1997 | Menezes et al. | |
| 5,684,560 A | 11/1997 | Roffman et al. | |
| 5,695,509 A | 12/1997 | El Hage | |
| 5,702,440 A | 12/1997 | Portney | |
| 5,713,958 A | 2/1998 | Weiser | |
| 5,716,403 A | 2/1998 | Tran et al. | |
| 5,725,576 A | 3/1998 | Fedorov et al. | |
| 5,728,155 A | 3/1998 | Anello et al. | |
| 5,760,871 A | 6/1998 | Kosoburd et al. | |
| 5,766,244 A | 6/1998 | Binder | |
| 5,769,890 A | 6/1998 | McDonald | |
| 5,770,125 A | 6/1998 | O'Connor et al. | |
| 5,776,191 A | 7/1998 | Mazzocco | |
| 5,776,192 A | 7/1998 | McDonald | |
| 5,800,533 A | 9/1998 | Eggleston et al. | |
| 5,814,103 A | 9/1998 | Lipshitz et al. | |
| 5,824,074 A | 10/1998 | Koch | |
| 5,843,188 A | 12/1998 | McDonald | |
| 5,847,802 A | 12/1998 | Menezes et al. | |
| 5,864,378 A | 1/1999 | Portney | |
| 5,869,549 A | 2/1999 | Christ et al. | |
| RE36,150 E | 3/1999 | Gupta | |
| 5,876,441 A | 3/1999 | Shibuya | |
| 5,876,442 A | 3/1999 | Lipshitz et al. | |
| 5,885,279 A | 3/1999 | Bretton | |
| 5,895,422 A | 4/1999 | Hauber | |
| 5,898,473 A | 4/1999 | Seidner et al. | |
| 5,928,283 A | 7/1999 | Gross et al. | |
| 5,929,969 A | 7/1999 | Roffman | |
| 5,968,094 A | 10/1999 | Werblin et al. | |
| 5,984,962 A | 11/1999 | Anello et al. | |
| 6,013,101 A | 1/2000 | Israel | |
| 6,015,435 A | 1/2000 | Valunin et al. | |
| 6,050,970 A | 4/2000 | Baerveldt | |
| 6,051,024 A | 4/2000 | Cumming | |
| 6,063,118 A | 5/2000 | Nagamoto | |
| 6,083,261 A | 7/2000 | Callahan et al. | |
| 6,090,141 A | 7/2000 | Lindstrom | |
| 6,096,078 A | 8/2000 | McDonald | |
| 6,102,946 A | 8/2000 | Nigam | |
| 6,106,553 A | 8/2000 | Feingold | |
| 6,106,554 A | 8/2000 | Bretton | |
| 6,110,202 A | 8/2000 | Barraquer et al. | |
| 6,113,633 A | 9/2000 | Portney | |
| 6,117,171 A | 9/2000 | Skottun | |
| 6,120,538 A | 9/2000 | Rizzo, III et al. | |
| 6,136,026 A | 10/2000 | Israel | |
| 6,139,576 A | 10/2000 | Doyle et al. | |
| 6,152,958 A | 11/2000 | Nordan | |
| 6,162,249 A | 12/2000 | Deacon et al. | |
| 6,176,878 B1 | 1/2001 | Gwon et al. | |
| 6,186,148 B1 | 2/2001 | Okada | |
| 6,197,058 B1 | 3/2001 | Portney | |
| 6,197,059 B1 | 3/2001 | Cumming | |
| 6,200,342 B1 * | 3/2001 | Tassignon | A61F 2/1602 623/6.37 |
| 6,210,005 B1 | 4/2001 | Portney | |
| 6,217,612 B1 | 4/2001 | Woods | |
| 6,221,105 B1 | 4/2001 | Portney | |
| 6,224,628 B1 | 5/2001 | Callahan et al. | |
| 6,228,115 B1 | 5/2001 | Hoffmann et al. | |
| 6,231,603 B1 | 5/2001 | Lang et al. | |
| 6,238,433 B1 | 5/2001 | Portney | |
| 6,241,777 B1 | 6/2001 | Kellan | |
| 6,251,312 B1 | 6/2001 | Phan et al. | |
| 6,258,123 B1 | 7/2001 | Young et al. | |
| 6,261,321 B1 | 7/2001 | Kellan | |
| 6,277,146 B1 | 8/2001 | Peyman et al. | |
| 6,277,147 B1 | 8/2001 | Christ et al. | |
| 6,280,471 B1 | 8/2001 | Peyman et al. | |
| 6,299,641 B1 | 10/2001 | Woods | |
| 6,302,911 B1 | 10/2001 | Hanna | |
| 6,322,213 B1 | 11/2001 | Altieri et al. | |
| 6,322,589 B1 | 11/2001 | Cumming | |
| 6,327,772 B1 | 12/2001 | Zadno-Azizi et al. | |
| 6,342,073 B1 | 1/2002 | Cumming et al. | |
| 6,358,280 B1 | 3/2002 | Herrick | |
| 6,364,906 B1 | 4/2002 | Baikoff et al. | |
| 6,387,126 B1 | 5/2002 | Cumming | |
| 6,399,734 B1 | 6/2002 | Hodd et al. | |
| 6,406,494 B1 | 6/2002 | Laguette et al. | |
| 6,423,094 B1 | 7/2002 | Sarfarazi | |
| 6,425,917 B1 | 7/2002 | Blake | |
| 6,443,985 B1 | 9/2002 | Woods | |
| 6,450,642 B1 | 9/2002 | Jethmalani et al. | |
| 6,454,802 B1 | 9/2002 | Bretton et al. | |
| 6,457,826 B1 | 10/2002 | Lett | |
| 6,464,725 B2 | 10/2002 | Skotton et al. | |
| 6,468,306 B1 | 10/2002 | Paul et al. | |
| 6,474,814 B1 | 11/2002 | Griffin | |
| 6,475,240 B1 | 11/2002 | Paul | |
| 6,478,821 B1 | 11/2002 | Laguette et al. | |
| 6,485,516 B2 | 11/2002 | Boehm | |
| 6,488,708 B2 | 12/2002 | Sarfarazi | |
| 6,494,911 B2 | 12/2002 | Cumming | |
| 6,503,276 B2 | 1/2003 | Lang et al. | |
| 6,517,577 B1 | 2/2003 | Callahan et al. | |
| 6,524,340 B2 | 2/2003 | Israel | |
| 6,533,813 B1 | 3/2003 | Lin et al. | |
| 6,533,814 B1 | 3/2003 | Jansen | |
| 6,536,899 B1 | 3/2003 | Fiala | |
| 6,547,822 B1 | 4/2003 | Lang | |
| 6,551,354 B1 | 4/2003 | Ghazizadeh et al. | |
| 6,554,859 B1 | 4/2003 | Lang et al. | |
| 6,558,420 B2 | 5/2003 | Green | |
| 6,559,317 B2 | 5/2003 | Hupperts et al. | |
| 6,589,550 B1 | 7/2003 | Hodd et al. | |
| 6,592,621 B1 | 7/2003 | Domino | |
| 6,598,606 B2 | 7/2003 | Terwee et al. | |
| 6,599,317 B1 | 7/2003 | Weinschenk, III et al. | |
| 6,609,793 B2 | 8/2003 | Norrby et al. | |
| 6,616,691 B1 | 9/2003 | Tran | |
| 6,616,692 B1 | 9/2003 | Glick et al. | |
| 6,616,693 B1 | 9/2003 | Nguyen | |
| 6,638,305 B2 | 10/2003 | Laguette | |
| 6,638,306 B2 | 10/2003 | Cumming | |
| 6,645,246 B1 | 11/2003 | Weinschenk, III et al. | |
| 6,660,035 B1 | 12/2003 | Lang et al. | |
| 6,685,315 B1 | 2/2004 | De | |
| 6,695,881 B2 | 2/2004 | Peng et al. | |
| 6,721,104 B2 | 4/2004 | Schachar et al. | |
| 6,730,123 B1 | 5/2004 | Klopotek | |
| 6,749,633 B1 | 6/2004 | Lorenzo et al. | |
| 6,749,634 B2 | 6/2004 | Hanna | |
| 6,761,737 B2 | 7/2004 | Zadno-Azizi et al. | |
| 6,764,511 B2 | 7/2004 | Zadno-Azizi et al. | |
| 6,767,363 B1 | 7/2004 | Bandhauer et al. | |
| 6,786,934 B2 | 9/2004 | Zadno-Azizi et al. | |
| 6,818,017 B1 | 11/2004 | Shu | |
| 6,818,158 B2 | 11/2004 | Pham et al. | |
| 6,827,738 B2 | 12/2004 | Willis et al. | |
| 6,836,374 B2 * | 12/2004 | Esch | A61F 2/16 359/665 |
| 6,846,326 B2 | 1/2005 | Zadno-Azizi et al. | |
| 6,855,164 B2 | 2/2005 | Glazier | |
| 6,858,040 B2 | 2/2005 | Nguyen et al. | |
| 6,884,261 B2 | 4/2005 | Zadno-Azizi et al. | |
| 6,884,262 B2 | 4/2005 | Brady et al. | |
| 6,884,263 B2 | 4/2005 | Valyunin et al. | |

(56) References Cited

U.S. PATENT DOCUMENTS

| | | | |
|---|---|---|---|
| 6,899,732 B2 | 5/2005 | Zadno-Azizi et al. | |
| 6,926,736 B2 | 8/2005 | Peng et al. | |
| 6,930,838 B2 | 8/2005 | Schachar | |
| 6,932,839 B1 | 8/2005 | Kamerling et al. | |
| 6,942,695 B1 | 9/2005 | Chapoy et al. | |
| 6,966,649 B2* | 11/2005 | Shadduck | A61F 2/145 351/159.74 |
| 7,018,409 B2 | 3/2006 | Glick et al. | |
| 7,021,760 B2 | 4/2006 | Newman | |
| 7,025,783 B2 | 4/2006 | Brady et al. | |
| 7,041,134 B2 | 5/2006 | Nguyen et al. | |
| 7,073,906 B1 | 7/2006 | Portney | |
| 7,087,080 B2 | 8/2006 | Zadno-Azizi et al. | |
| 7,097,660 B2 | 8/2006 | Portney | |
| 7,118,596 B2 | 10/2006 | Zadno-Azizi et al. | |
| 7,118,597 B2 | 10/2006 | Miller et al. | |
| 7,122,053 B2 | 10/2006 | Esch | |
| 7,125,422 B2 | 10/2006 | Woods et al. | |
| 7,150,759 B2 | 12/2006 | Paul et al. | |
| 7,179,292 B2 | 2/2007 | Worst et al. | |
| 7,182,780 B2 | 2/2007 | Terwee et al. | |
| 7,186,266 B2 | 3/2007 | Peyman | |
| 7,188,949 B2 | 3/2007 | Bandhauer et al. | |
| 7,198,640 B2 | 4/2007 | Nguyen | |
| 7,217,288 B2 | 5/2007 | Esch et al. | |
| 7,220,279 B2 | 5/2007 | Nun | |
| 7,223,288 B2 | 5/2007 | Zhang et al. | |
| 7,226,478 B2 | 6/2007 | Ting et al. | |
| 7,238,201 B2 | 7/2007 | Portney et al. | |
| 7,247,168 B2 | 7/2007 | Esch et al. | |
| 7,261,737 B2 | 8/2007 | Esch et al. | |
| 7,344,617 B2 | 3/2008 | Dubrow | |
| 7,452,362 B2 | 11/2008 | Zadno-Azizi et al. | |
| 7,452,378 B2 | 11/2008 | Zadno-Azizi et al. | |
| 7,503,938 B2 | 3/2009 | Phillips | |
| 7,615,056 B2 | 11/2009 | Ayton et al. | |
| 7,645,300 B2 | 1/2010 | Tsai | |
| 7,662,180 B2 | 2/2010 | Paul et al. | |
| 7,744,603 B2 | 6/2010 | Zadno-Azizi et al. | |
| 7,744,646 B2 | 6/2010 | Zadno-Azizi et al. | |
| 7,815,678 B2 | 10/2010 | Ben Nun | |
| 7,922,326 B2 | 4/2011 | Bandhauer et al. | |
| 8,034,108 B2 | 10/2011 | Bumbalough | |
| 8,052,752 B2 | 11/2011 | Woods et al. | |
| 8,343,217 B2 | 1/2013 | Bumbalough | |
| 9,198,752 B2* | 12/2015 | Woods | A61F 2/1613 |
| 9,277,987 B2* | 3/2016 | Smiley | A61F 2/1635 |
| 9,364,318 B2* | 6/2016 | Beer | A61F 2/1624 |
| 9,433,498 B2* | 9/2016 | Masket | A61F 2/1613 |
| 2001/0001836 A1 | 5/2001 | Cumming | |
| 2001/0004708 A1 | 6/2001 | Nagai | |
| 2001/0018612 A1 | 8/2001 | Carson et al. | |
| 2001/0039451 A1 | 11/2001 | Barnett | |
| 2001/0044657 A1 | 11/2001 | Kellan | |
| 2002/0004682 A1 | 1/2002 | Zhou et al. | |
| 2002/0011167 A1 | 1/2002 | Figov et al. | |
| 2002/0072796 A1 | 6/2002 | Hoffmann et al. | |
| 2002/0103536 A1 | 8/2002 | Landreville et al. | |
| 2002/0111678 A1 | 8/2002 | Zadno-Azizi et al. | |
| 2002/0116058 A1 | 8/2002 | Zadno-Azizi et al. | |
| 2002/0120329 A1 | 8/2002 | Lang et al. | |
| 2002/0151973 A1 | 10/2002 | Arita et al. | |
| 2002/0161434 A1 | 10/2002 | Laguette et al. | |
| 2002/0188351 A1* | 12/2002 | Laguette | 623/6.24 |
| 2002/0193876 A1 | 12/2002 | Lang et al. | |
| 2003/0002404 A1 | 1/2003 | Maekawa | |
| 2003/0004569 A1 | 1/2003 | Haefliger | |
| 2003/0013073 A1 | 1/2003 | Duncan et al. | |
| 2003/0020425 A1 | 1/2003 | Ricotti | |
| 2003/0033013 A1 | 2/2003 | Callahan et al. | |
| 2003/0045933 A1 | 3/2003 | Brady | |
| 2003/0050696 A1 | 3/2003 | Cumming | |
| 2003/0050697 A1 | 3/2003 | Paul | |
| 2003/0060878 A1 | 3/2003 | Shadduck | |
| 2003/0060881 A1 | 3/2003 | Glick et al. | |
| 2003/0078657 A1 | 4/2003 | Zadno-Azizi et al. | |
| 2003/0078658 A1 | 4/2003 | Zadno-Azizi | |
| 2003/0083744 A1 | 5/2003 | Khoury | |
| 2003/0086057 A1 | 5/2003 | Cleveland | |
| 2003/0105522 A1 | 6/2003 | Glazier | |
| 2003/0109925 A1 | 6/2003 | Ghazizadeh et al. | |
| 2003/0109926 A1 | 6/2003 | Portney | |
| 2003/0114927 A1 | 6/2003 | Nagamoto | |
| 2003/0130732 A1 | 7/2003 | Sarfarazi | |
| 2003/0135272 A1 | 7/2003 | Brady et al. | |
| 2003/0149480 A1 | 8/2003 | Shadduck | |
| 2003/0158599 A1 | 8/2003 | Brady et al. | |
| 2003/0187504 A1 | 10/2003 | Weinschenk et al. | |
| 2003/0187505 A1 | 10/2003 | Liao | |
| 2003/0204254 A1 | 10/2003 | Peng et al. | |
| 2003/0204255 A1* | 10/2003 | Peng | A61F 2/1613 623/6.34 |
| 2004/0002757 A1 | 1/2004 | Lai et al. | |
| 2004/0010496 A1 | 1/2004 | Behrendt et al. | |
| 2004/0014049 A1 | 1/2004 | Cowsert et al. | |
| 2004/0015236 A1 | 1/2004 | Sarfarazi | |
| 2004/0034415 A1 | 2/2004 | Terwee et al. | |
| 2004/0039446 A1 | 2/2004 | McNicholas | |
| 2004/0054408 A1 | 3/2004 | Glick et al. | |
| 2004/0082993 A1 | 4/2004 | Woods | |
| 2004/0082994 A1 | 4/2004 | Woods et al. | |
| 2004/0082995 A1 | 4/2004 | Woods | |
| 2004/0106992 A1 | 6/2004 | Lang et al. | |
| 2004/0111153 A1 | 6/2004 | Woods et al. | |
| 2004/0117013 A1 | 6/2004 | Schachar | |
| 2004/0148023 A1 | 7/2004 | Shu | |
| 2004/0156014 A1 | 8/2004 | Piers et al. | |
| 2004/0158322 A1 | 8/2004 | Shen | |
| 2004/0167621 A1 | 8/2004 | Peyman | |
| 2004/0181279 A1 | 9/2004 | Nun | |
| 2004/0215340 A1 | 10/2004 | Messner et al. | |
| 2004/0230299 A1 | 11/2004 | Simpson et al. | |
| 2004/0230300 A1 | 11/2004 | Bandhauer et al. | |
| 2004/0236423 A1 | 11/2004 | Zhang et al. | |
| 2004/0249456 A1 | 12/2004 | Cumming | |
| 2005/0018504 A1 | 1/2005 | Marinelli et al. | |
| 2005/0021139 A1 | 1/2005 | Shadduck | |
| 2005/0021140 A1 | 1/2005 | Liao | |
| 2005/0027354 A1 | 2/2005 | Brady et al. | |
| 2005/0038510 A1 | 2/2005 | Portney et al. | |
| 2005/0060032 A1 | 3/2005 | Magnante et al. | |
| 2005/0085906 A1 | 4/2005 | Hanna | |
| 2005/0085907 A1* | 4/2005 | Hanna | A61F 2/1613 623/6.37 |
| 2005/0099597 A1 | 5/2005 | Sandstedt et al. | |
| 2005/0125056 A1 | 6/2005 | Deacon et al. | |
| 2005/0125057 A1 | 6/2005 | Cumming | |
| 2005/0125058 A1 | 6/2005 | Cumming et al. | |
| 2005/0125059 A1 | 6/2005 | Pinchuk et al. | |
| 2005/0131535 A1 | 6/2005 | Woods | |
| 2005/0137703 A1 | 6/2005 | Chen | |
| 2005/0234547 A1 | 10/2005 | Nguyen et al. | |
| 2005/0246019 A1 | 11/2005 | Blake et al. | |
| 2005/0267575 A1 | 12/2005 | Nguyen et al. | |
| 2005/0288785 A1 | 12/2005 | Portney et al. | |
| 2006/0030938 A1 | 2/2006 | Altmann | |
| 2006/0064162 A1 | 3/2006 | Klima | |
| 2006/0095127 A1 | 5/2006 | Feingold et al. | |
| 2006/0098162 A1 | 5/2006 | Bandhauer et al. | |
| 2006/0100703 A1 | 5/2006 | Evans et al. | |
| 2006/0111776 A1 | 5/2006 | Glick et al. | |
| 2006/0116764 A1 | 6/2006 | Simpson | |
| 2006/0116765 A1 | 6/2006 | Blake et al. | |
| 2006/0149369 A1* | 7/2006 | Cumming | A61F 2/1613 623/6.37 |
| 2006/0178741 A1 | 8/2006 | Zadno-Azizi et al. | |
| 2006/0184244 A1 | 8/2006 | Nguyen et al. | |
| 2006/0209430 A1 | 9/2006 | Spivey | |
| 2006/0209431 A1 | 9/2006 | Spivey | |
| 2006/0235513 A1 | 10/2006 | Price, Jr. | |
| 2006/0238702 A1 | 10/2006 | Glick et al. | |
| 2006/0259139 A1 | 11/2006 | Zadno-Azizi et al. | |
| 2006/0271187 A1 | 11/2006 | Zadno-Azizi et al. | |
| 2007/0032866 A1 | 2/2007 | Portney | |

(56) References Cited

U.S. PATENT DOCUMENTS

| | | | |
|---|---|---|---|
| 2007/0050025 A1 | 3/2007 | Nguyen et al. | |
| 2007/0067872 A1 | 3/2007 | Mittendorf et al. | |
| 2007/0078515 A1 | 4/2007 | Brady | |
| 2007/0088433 A1 | 4/2007 | Esch et al. | |
| 2007/0100444 A1 | 5/2007 | Brady et al. | |
| 2007/0100445 A1 | 5/2007 | Shadduck | |
| 2007/0106377 A1 | 5/2007 | Smith et al. | |
| 2007/0106379 A1 | 5/2007 | Messner | |
| 2007/0106381 A1 | 5/2007 | Blake | |
| 2007/0108643 A1 | 5/2007 | Zadno-Azizi et al. | |
| 2007/0123591 A1 | 5/2007 | Kuppuswamy et al. | |
| 2007/0129798 A1 | 6/2007 | Chawdhary | |
| 2007/0135915 A1 | 6/2007 | Klima | |
| 2007/0156236 A1 | 7/2007 | Stenger | |
| 2007/0213817 A1* | 9/2007 | Esch et al. | 623/6.13 |
| 2007/0244561 A1* | 10/2007 | Ben Nun | 623/6.37 |
| 2007/0258143 A1 | 11/2007 | Portney | |
| 2007/0260309 A1 | 11/2007 | Richardson | |
| 2007/0282247 A1 | 12/2007 | Desai et al. | |
| 2007/0299487 A1 | 12/2007 | Shadduck | |
| 2008/0004699 A1 | 1/2008 | Ben Nun | |
| 2008/0125790 A1 | 5/2008 | Tsai et al. | |
| 2008/0140192 A1 | 6/2008 | Humayun et al. | |
| 2008/0161913 A1 | 7/2008 | Brady et al. | |
| 2008/0161914 A1 | 7/2008 | Brady et al. | |
| 2008/0300680 A1 | 12/2008 | Joshua | |
| 2009/0012609 A1 | 1/2009 | Geraghty et al. | |
| 2009/0234448 A1 | 9/2009 | Weeber et al. | |
| 2009/0248154 A1* | 10/2009 | Dell | A61F 2/1613 623/6.46 |
| 2010/0057203 A1 | 3/2010 | Glick et al. | |
| 2010/0228346 A1 | 9/2010 | Esch | |
| 2011/0035001 A1 | 2/2011 | Woods | |
| 2011/0251686 A1* | 10/2011 | Masket | A61F 2/1613 623/6.43 |
| 2012/0046744 A1 | 2/2012 | Woods et al. | |
| 2015/0173890 A1* | 6/2015 | Portney | A61F 2/1618 623/6.13 |
| 2016/0220351 A1* | 8/2016 | Dorronsoro D Az | A61F 2/1648 |

FOREIGN PATENT DOCUMENTS

| | | |
|---|---|---|
| CH | 681687 A5 | 5/1993 |
| DE | 2702117 A1 | 7/1978 |
| DE | 3246306 A1 | 6/1984 |
| DE | 4038088 A1 | 6/1992 |
| DE | 19501444 A1 | 7/1996 |
| DE | 19951148 A1 | 4/2001 |
| DE | 20109306 U1 | 8/2001 |
| DE | 10059482 A1 | 6/2002 |
| DE | 10125829 A1 | 11/2002 |
| EP | 64812 A2 | 11/1982 |
| EP | 162573 A2 | 11/1985 |
| EP | 212616 A2 | 3/1987 |
| EP | 246216 A2 | 11/1987 |
| EP | 328117 A2 | 8/1989 |
| EP | 329981 A1 | 8/1989 |
| EP | 331457 A2 | 9/1989 |
| EP | 336877 A1 | 10/1989 |
| EP | 0337390 A2 | 10/1989 |
| EP | 342895 A2 | 11/1989 |
| EP | 351471 A2 | 1/1990 |
| EP | 356050 A1 | 2/1990 |
| EP | 337390 A3 | 5/1990 |
| EP | 402825 A1 | 12/1990 |
| EP | 420549 A2 | 4/1991 |
| EP | 470811 A2 | 2/1992 |
| EP | 478929 A1 | 4/1992 |
| EP | 480748 A1 | 4/1992 |
| EP | 488835 A1 | 6/1992 |
| EP | 492126 A2 | 7/1992 |
| EP | 507292 A1 | 10/1992 |
| EP | 566170 A1 | 10/1993 |
| EP | 601845 A1 | 6/1994 |
| EP | 605841 A1 | 7/1994 |
| EP | 691109 A1 | 1/1996 |
| EP | 766540 A1 | 4/1997 |
| EP | 779063 A1 | 6/1997 |
| EP | 780718 A1 | 6/1997 |
| EP | 0891102 A2 | 2/1999 |
| EP | 897702 A2 | 2/1999 |
| EP | 766540 B1 | 8/1999 |
| EP | 1108402 A2 | 6/2001 |
| EP | 1321112 A1 | 6/2003 |
| EP | 1647241 A2 | 4/2006 |
| EP | 1424049 B1 | 6/2009 |
| EP | 2523632 A2 | 11/2012 |
| FR | 488835 A | 11/1918 |
| FR | 2666504 A1 | 3/1992 |
| FR | 2666735 A1 | 3/1992 |
| FR | 2681524 A1 | 3/1993 |
| FR | 2745711 A1 | 9/1997 |
| FR | 2778093 A1 | 11/1999 |
| FR | 2784575 A1 | 4/2000 |
| GB | 939016 A | 10/1963 |
| GB | 2058391 A | 4/1981 |
| GB | 2124500 A | 2/1984 |
| GB | 2129155 A | 5/1984 |
| GB | 2146791 A | 4/1985 |
| GB | 2192291 A | 1/1988 |
| GB | 2215076 A | 9/1989 |
| JP | 0211134 | 1/1990 |
| JP | 2126847 A | 5/1990 |
| JP | H06508279 | 9/1994 |
| JP | 7005399 A2 | 1/1995 |
| JP | 7222760 A2 | 8/1995 |
| JP | H09501856 A | 2/1997 |
| JP | H09502542 A | 3/1997 |
| JP | 10000211 A2 | 1/1998 |
| JP | H11500030 A | 1/1999 |
| JP | 11047168 A2 | 2/1999 |
| JP | 2000508588 T2 | 7/2000 |
| JP | 2003513704 T | 4/2003 |
| JP | 2003190193 A | 7/2003 |
| JP | 2003522592 T2 | 7/2003 |
| JP | 2003525694 A | 9/2003 |
| RU | 2014038 C1 | 6/1994 |
| RU | 2014039 C1 | 6/1994 |
| WO | 8404449 A1 | 11/1984 |
| WO | WO8603961 A1 | 7/1986 |
| WO | WO8700299 A1 | 1/1987 |
| WO | WO8707496 A1 | 12/1987 |
| WO | 8803961 A1 | 6/1988 |
| WO | WO8902251 A1 | 3/1989 |
| WO | WO8911672 A1 | 11/1989 |
| WO | 8911872 A1 | 12/1989 |
| WO | WO9000889 A1 | 2/1990 |
| WO | 9109336 A1 | 6/1991 |
| WO | 9302639 A1 | 2/1993 |
| WO | WO9305733 A1 | 4/1993 |
| WO | WO9416648 A1 | 8/1994 |
| WO | WO9503783 A1 | 2/1995 |
| WO | WO9610968 A1 | 4/1996 |
| WO | WO9615734 A2 | 5/1996 |
| WO | WO9625126 A1 | 8/1996 |
| WO | WO9712272 A1 | 4/1997 |
| WO | WO9727825 A1 | 8/1997 |
| WO | WO9743984 A1 | 11/1997 |
| WO | 9805273 A1 | 2/1998 |
| WO | 9821621 A1 | 5/1998 |
| WO | 9635398 A1 | 11/1998 |
| WO | 9849594 A1 | 11/1998 |
| WO | WO9856315 A1 | 12/1998 |
| WO | 9903427 A1 | 1/1999 |
| WO | 9907309 A1 | 2/1999 |
| WO | 9920206 A1 | 4/1999 |
| WO | 9921491 A1 | 5/1999 |
| WO | 9929266 A1 | 6/1999 |
| WO | 0021467 A1 | 4/2000 |
| WO | WO0027315 A1 | 5/2000 |
| WO | 0035379 A1 | 6/2000 |
| WO | 0046629 A1 | 8/2000 |
| WO | 0059407 A1 | 10/2000 |

(56) References Cited

FOREIGN PATENT DOCUMENTS

| | | |
|---|---|---|
| WO | WO0061036 A1 | 10/2000 |
| WO | 0066037 A1 | 11/2000 |
| WO | 0066040 A1 | 11/2000 |
| WO | 0066041 A1 | 11/2000 |
| WO | WO0066039 A1 | 11/2000 |
| WO | 02098328 A1 | 12/2000 |
| WO | 0108605 A1 | 2/2001 |
| WO | 0119289 A1 | 3/2001 |
| WO | WO0119288 A1 | 3/2001 |
| WO | 0128144 A1 | 4/2001 |
| WO | 0134061 A1 | 5/2001 |
| WO | WO0134066 A1 | 5/2001 |
| WO | WO0134067 A1 | 5/2001 |
| WO | 0156510 A1 | 8/2001 |
| WO | 0160286 A1 | 8/2001 |
| WO | 0164135 A1 | 9/2001 |
| WO | 0164136 A2 | 9/2001 |
| WO | 0166042 A1 | 9/2001 |
| WO | 0182839 A1 | 11/2001 |
| WO | 0189816 A1 | 11/2001 |
| WO | 0209620 A1 | 2/2002 |
| WO | 0212523 A2 | 2/2002 |
| WO | WO0219949 A2 | 3/2002 |
| WO | 02058391 A2 | 7/2002 |
| WO | 02071983 A1 | 9/2002 |
| WO | 03009051 A2 | 1/2003 |
| WO | 03015657 A2 | 2/2003 |
| WO | WO03015669 A1 | 2/2003 |
| WO | WO03034949 A2 | 5/2003 |
| WO | 03049646 A2 | 6/2003 |
| WO | 03057081 A2 | 7/2003 |
| WO | 03059196 A2 | 7/2003 |
| WO | WO03059208 A2 | 7/2003 |
| WO | WO03075810 A1 | 9/2003 |
| WO | 03084441 A1 | 10/2003 |
| WO | 03092552 A1 | 11/2003 |
| WO | 04000171 A1 | 12/2003 |
| WO | 04020549 A1 | 3/2004 |
| WO | 04037127 A2 | 5/2004 |
| WO | 04073559 A1 | 9/2004 |
| WO | 05011531 A2 | 2/2005 |
| WO | 2005019871 A2 | 3/2005 |
| WO | WO2005018504 A1 | 3/2005 |
| WO | 03082147 A3 | 8/2005 |
| WO | 05084587 A2 | 9/2005 |
| WO | WO2005115278 A1 | 12/2005 |
| WO | 06025726 A1 | 3/2006 |
| WO | 06118452 A1 | 11/2006 |
| WO | WO2007040964 A1 | 4/2007 |
| WO | WO2007067872 A2 | 6/2007 |
| WO | 2008077795 A2 | 7/2008 |
| WO | 2008079671 A1 | 7/2008 |
| WO | 2008108524 A1 | 9/2008 |
| WO | 2009021327 A1 | 2/2009 |
| WO | 2010093823 A2 | 8/2010 |
| WO | 2011017322 A1 | 2/2011 |
| ZA | 0888414 | 11/1988 |

OTHER PUBLICATIONS

"DVD titled "New elliptical accommodative IOL for cataract surgery" shown at ASCRS Symposium on Apr. 10, 1999."
English translation of WO93/05733A1.
Fechner P.U., et al., "Iris-Claw Lens In Phakic Eyes To Correct Hyperopia: Preliminary Study," Journal of Cataract and Refractive Surgery, 1998, vol. 24 (1), pp. 48-56.
International Search Report for Application No. PCT/US09/038466, mailed on Sep. 17, 2009, 2 pages.
Mandell R.B. "Contact Lens Practice", 4th Edition, Charles C. Thomas Publishers.
Menezo J.L., et al., "Endothelial Study of Iris-Claw Phakic Lens: Four Year Follow-Up," Journal of Cataract Refractive Surgery, 1998, vol. 24 (8), pp. 1039-1049.
U.S. Appl. No. 09/656,661, filed Sep. 7, 2000.
"Program from ASCRS Symposium showing video tape between Apr. 10-14, 1999, 2 pages."
Study Design of Nuvita, Mar. 20, 1997, 5 pages.
Thornton S., "Accommodation in Pseudophakia," 1991, pp. 159-162.
U.S. Appl. No. 10/280,918, filed Aug. 5, 2003.
U.S. Appl. No. 10/280,937, filed Oct. 25, 2005.
U.S. Appl. No. 09/721,072, filed Nov. 22, 2000.
Adler-Grinberg D., "Questioning Our Classical Understanding of Accommodation and Presbyopia," American Journal of Optometry & Physiological Optics, 1986, vol. 63 (7), pp. 571-580.
Altan-Yaycioglu R., et al., "Pseudo-accommodation with Intraocular Lenses Implanted in the Bag," Journal of Refractive Surgery, 2002, vol. 18 (3), pp. 271-275.
Chauvin-Opsia, Azurite ACL (0459).
Chiron, Clemente Optfit Model SP525, Brochure Translation, Jul. 12, 1998.
Cohen A.L., "Diffractive Bifocal Lens Design," Optometry and Vision Science, Jun. 1993, vol. 70 (6), pp. 461-468.
Cohen A.L., "Practical Design of a Bifocal Hologram Contact Lens or Intraocular Lens," Applied Optics, Jul. 1, 1992, vol. 31 (19), pp. 3750-3754.
European Search Report for Application No. EP09009432, dated Aug. 27, 2009, 2 pages.
European Search Report for Application No. EP09178394, dated Jan. 25, 2010, 2 pages.
European Search Report for Application No. EP10181797, dated Jan. 28, 2011, 2 pages.
European Search Report for Application No. EP11152227, dated Oct. 21, 2011, 7 pages.
Extended European Search Report for Application No. EP11152508, dated Oct. 25, 2011, 7 pages.
Foldable Intraocular Lens Implants and Small Incision Cataract Surgery, Ohio Valley Eye Physicians, 2004.
Hanita Lenses, Source Ocular Surgery News International, 1 page.
Hara T., et al., "Accommodative Intraocular Lens with Spring Action Part 1 Design and Placement in an Excised Animal Eye," Ophthalmic Surgery, 1990, vol. 21 (2), pp. 128-133.
Hecht E., et al., "Optics", 4th Edition, Addison-Wesley Publishing Company, 1979, pp. 188-190.
Holladay J.T., et al., "A Three-Part System for Refining Intraocular Lens Power Calculations," Journal of Cataract and Refractive Surgery, 1988, vol. 14 (1), pp. 17-24.
Holladay J.T., et al., "Analysis of Edge Glare Phenomena in Intraocular Lens Edge Designs," Journal of Cataract and Refractive Surgery, 1999, vol. 25 (6), pp. 748-752.
Iolab Corp., Source Ophthalmology Times, Mar. 15, 1995, 1 page.
Jacobi F.K., et al., "Bilateral Implantation of Asymmetrical Diffractive Multifocal Intraocular Lenses," Archives of Ophthalmology, 1999, vol. 117 (1), pp. 17-23.
Klien S.A., "Understanding the Diffractive Bifocal Contact Lens," Optometry and Vision Science, 1993, vol. 70 (6), pp. 439-460.
Kuchle M., et al., "Implantation of a New Accommodative Posterior Chamber Intraocular Lens," Journal of Refractive Surgery, 2002, vol. 18 (3), pp. 208-216.
Lane S.S., et al., "Polysulfone Intracorneal Lenses," International Ophthalmology Clinics, 1991, vol. 31 (1), pp. 37-46.
Mandell R.B., et al., "Mathematical Model of the Corneal Contour," 1965, School of Optometry, University of California, Berkeley, pp. 183-197.
Marron J.C., et al., "Higher-order Kinoforms," Computer and Optically Formed Holographic Optics, 1990, vol. 1211, pp. 62-66.
McCarey B.E., et al., "Modeling Glucose Distribution in The Cornea," Current Eye Research, 1990, vol. 9 (11), pp. 1025-1039.
Mediphacos Ltda, Ocular Surgery News International.
Office Action dated Jul. 19, 2011 for Japanese Application No. 2006526344 filed Sep. 10, 2004.
Opthalmed Inc., OMAC-260.
Pending Claims dated Jul. 29, 2009 for U.S. Appl. No. 11/618,411, filed Dec. 29, 2006.
Prosecution History for U.S. Appl. No. 10/958,871, filed Oct. 5, 2004.

(56) References Cited

OTHER PUBLICATIONS

Prosecution History for U.S. Appl. No. 11/057,705, filed Feb. 14, 2005.
Prosecution History for U.S. Appl. No. 11/195,422, filed Aug. 1, 2005.
Prosecution History for U.S. Appl. No. 11/426,888, filed Jun. 27, 2006.
Ramocki J.M., et al., "Foldable Posterior Chamber Intraocular Lens Implantation in the Absence of Capsular and Zonular Support," American Journal of Ophthalmology, 1999, vol. 127 (2), pp. 213-216.
Simonov A.N., et al., "Cubic Optical Elements for an Accommodative Intraocular Lens," Optics Express, 2006, vol. 14 (17), pp. 7757-7775.
Storz Opthalmics Inc., Model L122UV ACL.
Supplementary European Search Report for Application No. EP00980998, dated Sep. 11, 2007, 2 pages.
Supplementary European Search Report for Application No. EP02748257, dated Jun. 23, 2008, 2 pages.
Supplementary European Search Report for Application No. EP03777934, dated Jan. 26, 2010, 3 pages.
Supplementary European Search Report for Application No. EP03809651, dated Aug. 11, 2006, 2 pages.
Supplementary European Search Report for Application No. EP04814069, dated Jul. 12, 2007, 1 page.
Taylor B.N., ed., The International System of Units (SI), 1991, NIST Special Publication 330, 4 pages.
Tetz M., et al., "Evaluating and Defining the Sharpness of Intraocular Lenses: Part 1: Influence of Optic Design on the Growth of the Lens Epithelial Cells in Vitro," Journal of Cataract and Refractive Surgery, 2005, vol. 31 (11), pp. 2172-2179.
Universe IOL Center, Ocular Surgery News International.
Video presented by ASCRS Symposium of Cataracts IOL and Refractive Surgery at the ASOA Congress on Ophthalmic Practice Management. Clinical & Surgical Staff Program on Apr. 10-14, 1999 (VHS Tape).
World Optics Inc., Ophthalmology Times, Mar. 15, 1995.

* cited by examiner

SECTION B-B

SECTION B-B

SECTION B-B

INTRAOCULAR LENS HAVING A HAPTIC THAT INCLUDES A CAP

RELATED APPLICATIONS

This application is a continuation application of, and claims priority to, application Ser. No. 12/057,633, now U.S. Pat. No. 8,034,108 issued on Oct. 11, 2011, which is incorporated by reference in its entirety.

BACKGROUND OF THE INVENTION

Field of the Invention

This invention relates generally to intraocular lenses, and more specifically to accommodating intraocular lenses.

Description of the Related Art

A human eye can suffer diseases that impair a patient's vision. For instance, a cataract may increase the opacity of the lens, causing blindness. To restore the patient's vision, the diseased lens may be surgically removed and replaced with an artificial lens, known as an intraocular lens, or IOL. An IOL may also be used for presbyopic lens exchange.

The simplest IOLs have a single focal length, or, equivalently, a single power. Unlike the eye's natural lens, which can adjust its focal length within a particular range in a process known as accommodation, these single focal length IOLs cannot accommodate. As a result, objects at a particular position away from the eye appear in focus, while objects at an increasing distance away from that position appear increasingly blurred.

An improvement over the single focal length IOLs is an accommodating IOL, which can adjust its power within a particular range. More specifically, an accommodating intraocular lens may change its shape (power) and/or position, so that objects at prescribed distances will be clearly imaged at the plane of the retina. As a result, the patient can clearly focus on objects in a range of distances away from the eye, rather than at a single distance. This ability to accommodate is of tremendous benefit for the patient, and more closely approximates the patient's natural vision than a single focal length IOL.

When the eye focuses on a relatively distant object, the lens power is at the low end of the accommodation range, which may be referred to as the "far" power. When the eye focuses on a relatively close object, the lens power is at the high end of the accommodation range, which may be referred to as the "near" power. The accommodation range itself is defined as the near power minus the far power. In general, an accommodation range of 4 diopters is considered sufficient for most patients.

The human eye contains a structure known as the capsular bag, which surrounds the natural lens. The capsular bag is transparent, and serves to hold the lens. In the natural eye, accommodation is initiated by a series of zonular fibers, also known as zonules. The zonules are located in a relatively thick band mostly around the equator of the lens, and impart a largely radial force to the capsular bag that can alter the shape and/or the location of the natural lens and thereby change its power.

In a typical surgery in which the natural lens is removed from the eye, the lens material is typically broken up and vacuumed out of the eye, but the capsular bag is, left intact. The remaining capsular bag is extremely useful for an accommodating intraocular lens, in that the eye's natural accommodation is initiated at least in part by the zonules through the capsular bag. The capsular bag may be used to house an accommodating IOL, which in turn can change shape and/or shift in some manner to affect the power and/or the axial location of the image.

The IOL has an optic, which refracts light that passes through it and forms an image on the retina, and a haptic, which is a structure that mechanically couples the optic to the capsular bag. During accommodation, the zonules exert a force on the capsular bag, which in turn exerts a force on the optic. The force may be transmitted from the capsular bag directly to the optic, or from the capsular bag through the haptic to the optic.

A desirable optic for an accommodating IOL is one that distorts in response to a squeezing or expanding radial force applied largely to the equator of the optic (i.e., by pushing or pulling on or near the edge of the optic, circumferentially around the optic axis). Under the influence of a squeezing force, the optic bulges slightly in the axial direction, producing more steeply curved anterior and/or posterior faces, and producing an increase in the power of the optic. Likewise, an expanding radial force produces a decrease in the optic power by flattening the optic. This change in power is accomplished in a manner similar to that of the natural eye and is well adapted to accommodation. Furthermore, this method of changing the lens power reduces any undesirable pressures exerted on some of the structures in the eye.

One challenge in implementing such an optic is designing a suitable haptic to couple the optic to the capsular bag. The haptic should allow distortion of the optic in an efficient manner, so that a relatively small zonular force can produce a relatively large change in power and/or axial location of the image. This reduces fatigue on the eye, which is highly desirable.

Accordingly, there exists a need for an intraocular lens having a haptic with increased efficiency in converting a zonular force to a change in power and/or a change in axial location of the image.

BRIEF DESCRIPTION OF THE DRAWINGS

Embodiments of the present invention may be better understood from the following detailed description when read in conjunction with the accompanying drawings. Such embodiments, which are for illustrative purposes only, depict the novel and non-obvious aspects of the invention. The drawings include the following 20 figures, with like numerals indicating like parts.

DETAILED DESCRIPTION OF THE DRAWINGS

In a healthy human eye, the natural lens is housed in a structure known as the capsular bag. The capsular bag is driven by zonular fibers (also known as zonules) in the eye, which can compress and/or pull on the capsular bag to change its shape. The motions of the capsular bag distort the natural lens in order to change its power and/or the location of the image, so that the eye can focus on objects at varying distances away from the eye in a process known as accommodation.

For some people suffering from cataracts, the natural lens of the eye becomes clouded or opaque. If left untreated, the vision of the eye becomes degraded and blindness can occur in the eye. A standard treatment is surgery, during which the natural lens is broken up, removed, and replaced with a manufactured intraocular lens. Typically, the capsular bag is left intact in the eye, so that it may house the implanted intraocular lens.

Because the capsular bag is capable of motion, initiated by the zonules, it is desirable that the implanted intraocular lens change its power and/or the location of the image in a manner similar to that of the natural lens. Such an accommodating lens may produce vastly improved vision over a lens with a fixed power and location that does not accommodate.

Figure 1:
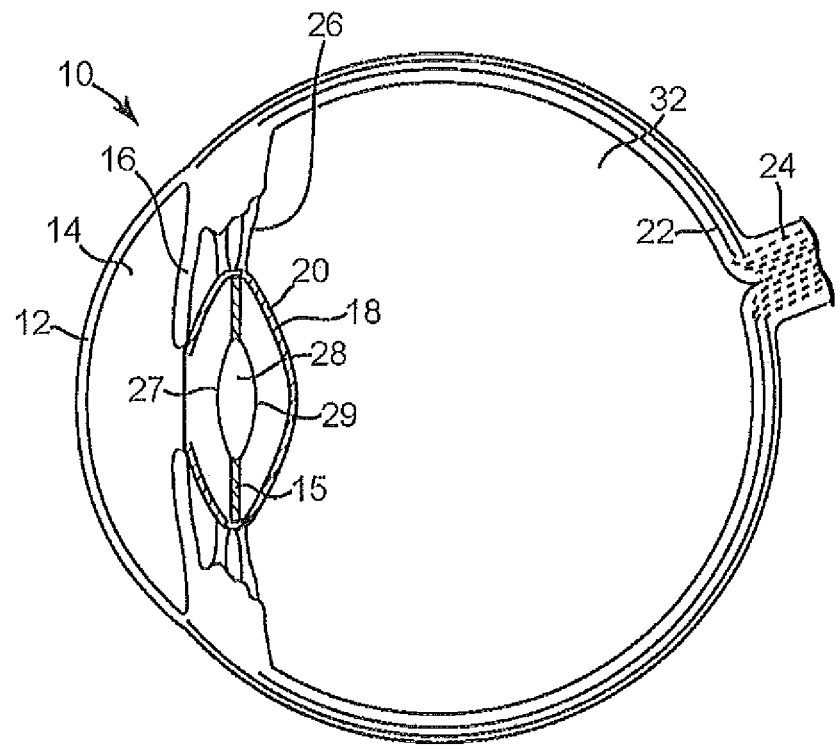
FIG. 1 is a plan drawing of a human eye having an implanted intraocular lens, in an accommodative "near" state.

FIG. 1 shows a human eye 10, after an accommodating intraocular lens according to an embodiment of the present invention has been implanted into the eye of a subject. Light enters from the left of FIG. 1, and passes through the cornea 12, the anterior chamber 14, the iris 16, and enters the capsular bag 18. Prior to surgery, the natural lens occupies essentially the entire interior of the capsular bag 18. After surgery, the capsular bag 18 houses the intraocular lens, in addition to a fluid that occupies the remaining volume and equalizes the pressure in the eye. The intraocular lens is described in more detail below. After passing through the intraocular lens, light exits the posterior wall 20 of the capsular bag 18, passes through the posterior chamber 32, and strikes the retina 22, which detects the light and converts it to a signal transmitted through the optic nerve 24 to the brain.

A well-corrected eye forms an image at the retina 22. If the lens has too much or too little power, the image shills axially along the optical axis away from the retina, toward or away from the lens. Note that the power required to focus on a close or near object is more than the power required to focus on a distant or far object. The difference between the "near" and "far" powers is known typically as the range of accommodation. A normal range of accommodation is about 4 diopters, which is considered sufficient for most patients.

The capsular bag is acted upon by the zonules 26, which distort the capsular bag 18 by compressing and/or stretching it radially in a relatively thick band about its equator. Experimentally, it is found that the zonules typically exert a total force of up to about 10 grains of force, which is distributed generally uniformly around the equator of the capsular bag 18. Although the range of zonule force may vary from patient to patient, it should be noted that for each patient, the range of accommodation is limited by the total force that the zonules 26 can exert. Therefore, it is highly desirable that the intraocular lens be configured to vary its power over the full range of accommodation, in response to this limited range of forces exerted by the zonules. In other words, it is desirable to have a relatively large change in power for a relatively small driving force.

Note that the lens may be designed so that its relaxed state is the "far" condition, sometimes referred to as "disaccommodative biased", the "near" condition, "accommodative biased", or some condition in between the two.

The intraocular lens itself has two primary components: an optic 28, which is made of a transparent, deformable and/or elastic material, and a haptic 15, which holds the optic 28 in place and mechanically transfers forces on the capsular bag 18 to the optic 28.

Note that either or both of the haptic 15 and optic 28 may include relatively complex structures that can blur the distinction between the two. For instance, the optic may be made from a soft material, and may include a harder shell-like coating on at least one of the opposite faces of the optic disposed about the optical axis, namely the anterior and/or posterior surfaces. This coating may be made from the same material as the haptic and may or may not be made integral with the haptic. One may argue that such a coating is part of the haptic, since it may be made from the same material as the haptic. Likewise, one may argue that it resides on an optical surface and plays a role in the focusing functions of the lens, and may therefore be considered part of the optic. For the purposes of this document, the strict distinction between haptic and optic is relatively unimportant, and any elements that share a role in the optical and mechanical functions of the lens may be considered to be part of the optic, part of the haptic, or both.

When the eye 10 is focused on a relatively close object, as shown in FIG. 1, the zonules 26 compress the capsular bag 18 in a relatively thick band about its equator. The capsular bag 18 changes shape, becoming thicker at its center and having more steeply curved sides. As a result of this action, the power of the lens increases (i.e., one or both of the radii of curvature can decrease, and/or the lens can become thicker, and/or the lens may also move axially), placing the image of the relatively close object at the retina 22. Note that if the lens could not accommodate, the image of the relatively close object would be located behind the retina, and would appear blurred.

Figure 2:
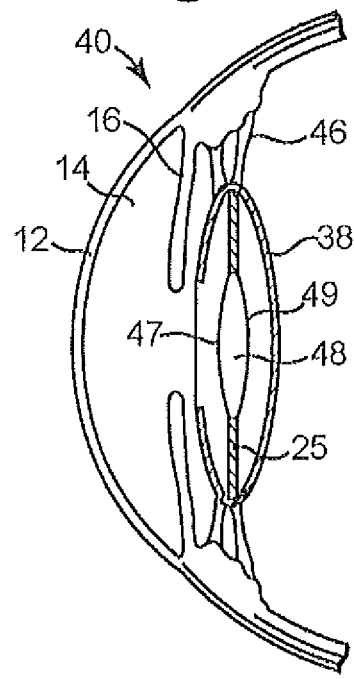
FIG. 2 is a plan drawing of the human eye of FIG. 1, in an accommodative "far" state.
Figure 3:
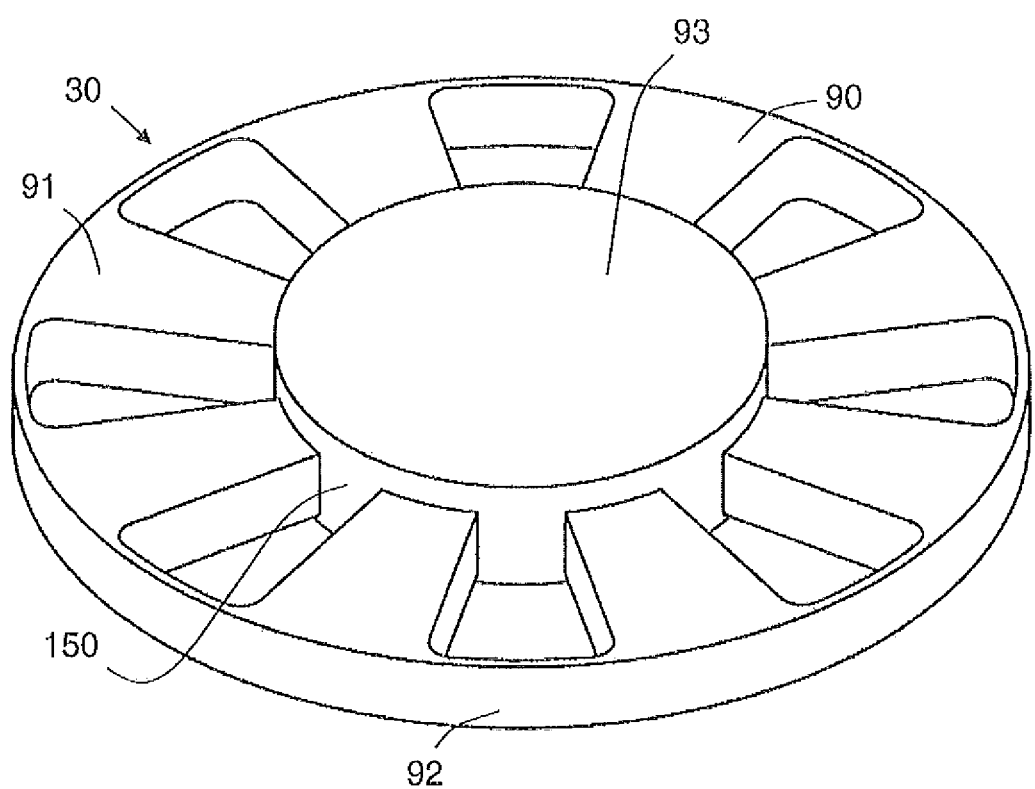
FIG. 3 is an anterior isometric drawing of a haptic/optic assembly.
Figure 4:
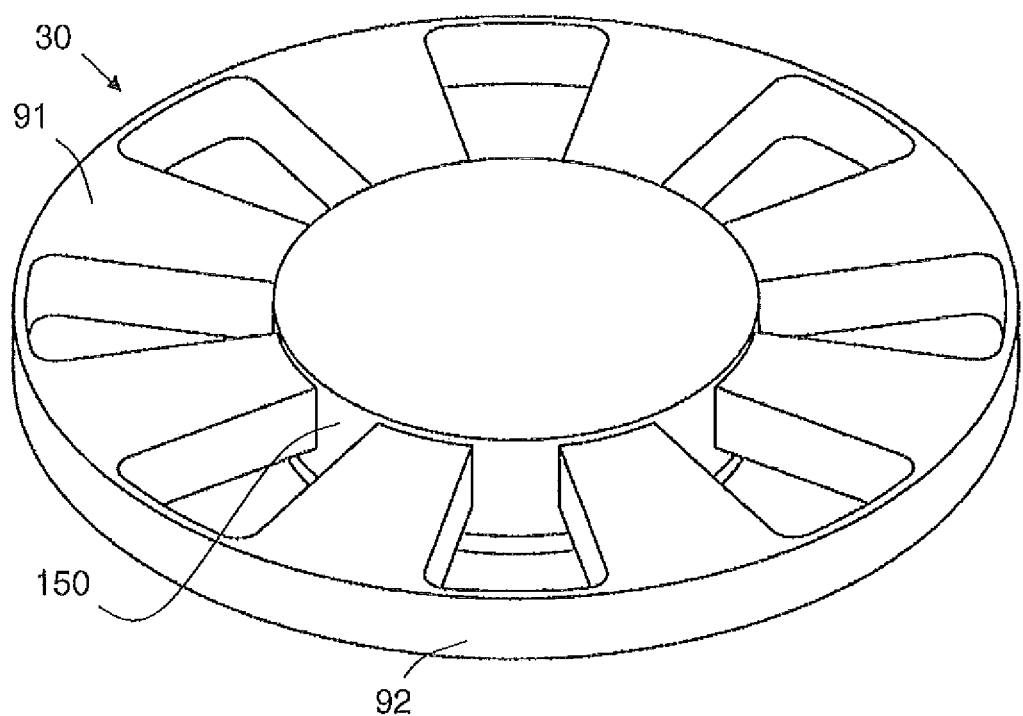
FIG. 4 is a posterior isometric drawing of a haptic/optic assembly.

FIG. 2 shows a portion of an eye 40 that is focused on a relatively distant object. The cornea 12 and anterior chamber 14 are typically unaffected by accommodation, and are generally similar to the corresponding elements in FIG. 1. To focus on the distant object, the zonules 46 retract and change the shape of the capsular bag 38, which becomes thinner at its center and has less steeply curved sides. This reduces the lens power by flattening (i.e., lengthening radii of curvature and/or thinning) the lens, placing the image of the relatively distant object at the retina (not shown).

In the illustrated embodiment of FIGS. 1 and 2, near and distant vision are both generally provided as the intraocular lens responds to shape changes in the capsular bag. In certain embodiments, the intraocular lens may be configured to have a disaccommodative bias, wherein the power of the optic 28 is generally selected to provide distant vision when haptic 50 and optic 28 are in a natural or unstressed state (i.e., when there are substantially no external forces on the intraocular lens). In such embodiments, the intraocular lens is in a natural state when the ciliary muscle is relaxed, thereby pulling on the zonules and capsular bag. In this state, the radius of curvature of the anterior face 47 and/or posterior face 49 are generally relatively large, which results in a relatively low lens power. For near vision the ciliary muscle contracts and the haptic 50 and optic 28 are compress by the capsular bag as tension on the zonules is reduced. In this stressed state of the optic 28, the radius of curvature is decreased, thus increasing the lens power.

In other embodiments, the intraocular lens may be configured to have an accommodative bias, wherein the power of the optic 28 is selected to provide near vision when haptic 50 and optic 28 are in a natural or unstressed state. In such embodiments, the intraocular lens is in a natural state when the ciliary muscle contracts to relax the zonules and capsular bag. In this state, the radius of curvature of the anterior face 47 and/or its posterior face 49 is relatively small, which results in a relatively high lens power. For distant vision, the ciliary muscle relax, which pulls on the zonules, capsular bag, the haptic 50, and optic 28. In this stressed state of the optic 28, the radius of curvature is increased, thus decreasing the lens power. Alternatively, the optic 28 may be selected to have an intermediate power between near and distant when in a natural or unstressed state. In such embodiments, the haptic 50 and optic 28 may be both compressed and stretched to provide near and distant vision, respectively.

Note that the specific degrees, of change in curvature of the anterior and posterior faces depend on the nominal curvatures. Although the optics 28 and 48 are drawn as bi-convex, they may also be plano-convex, meniscus or other lens shapes, where the anterior and posterior faces may each be convex, concave or planar. In all of these cases, the optic is compressed or expanded by essentially radial forces by the haptic to the edge and/or faces of the optic. In addition, the may be some axial movement of the optic. In some embodiments, the haptic is configured to transfer the generally symmetric radial forces symmetrically to the optic to deform the optic in a spherically symmetric way. However, in alternate embodiments the haptic is configured non-uniformly (e.g., having different material properties, thickness, dimensions, spacing, angles or curvatures), to allow for non-uniform transfer of forces by the haptic to the optic. For example, this could be used to combat astigmatism, coma or other asymmetric aberrations of the eye/lens system. The optics may optionally have one or more diffractive elements, one or more multifocal elements, and/or one or more aspheric elements.

An exemplary intraocular lens is shown in detail in FIGS. 3-20, which show a similar series of views for the haptic/optic assembly 30 (FIGS. 3-8), only the haptic 90 (FIGS. 9-14), and only the optic 150 (FIGS. 15-20). Each of the six figures for the haptic/optic assembly 30, the haptic 90 and optic 150 shows, in order, an anterior isometric drawing, a posterior isometric drawing, a front view drawing, a section view A-A drawing, a top view drawing and a section view B-B drawing.

The intraocular lens may be generally saucer- or capsule-shaped, lying essentially in a plane perpendicular to the optical axis of the lens. The haptic 90 may have an optional, generally circular outer edge 92 extending around the equator of the lens, which couples the lens to the capsular bag of the eye. Alternatively, there may be additional features and/or discontinuities along the outer edge 92.

Figure 7:
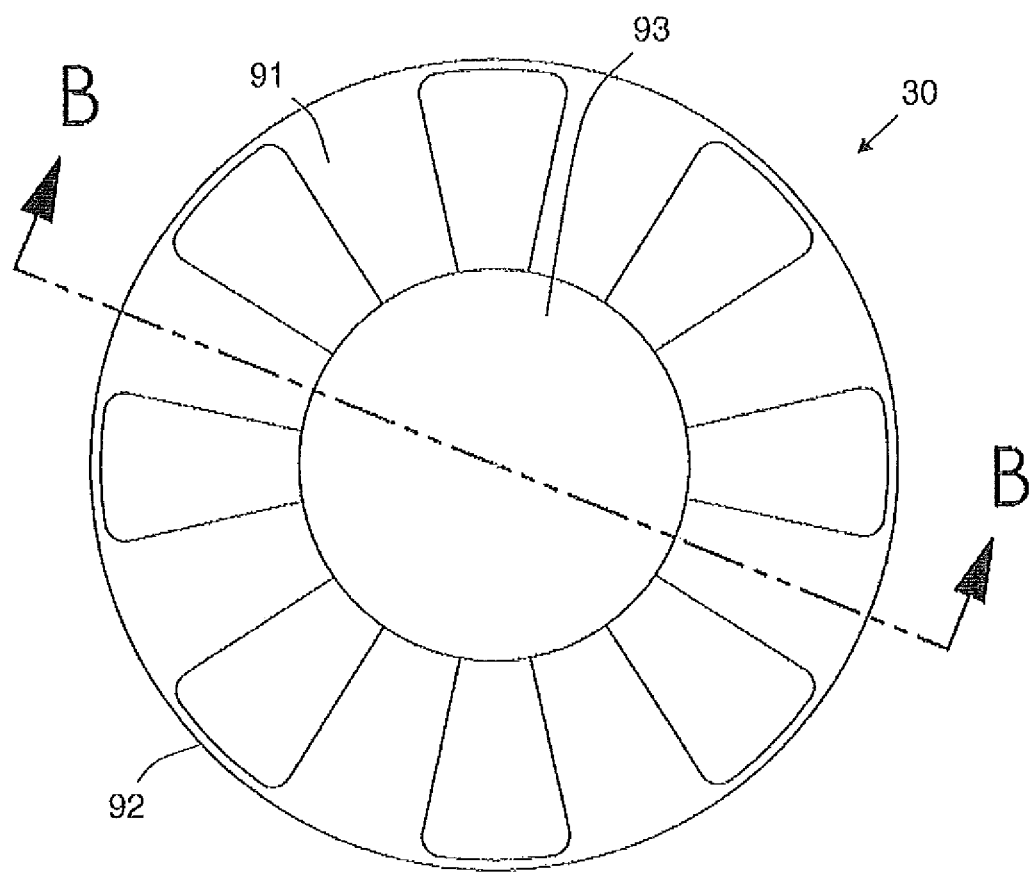
FIG. 7 is a top view drawing of a haptic/optic assembly.
Figure 8:
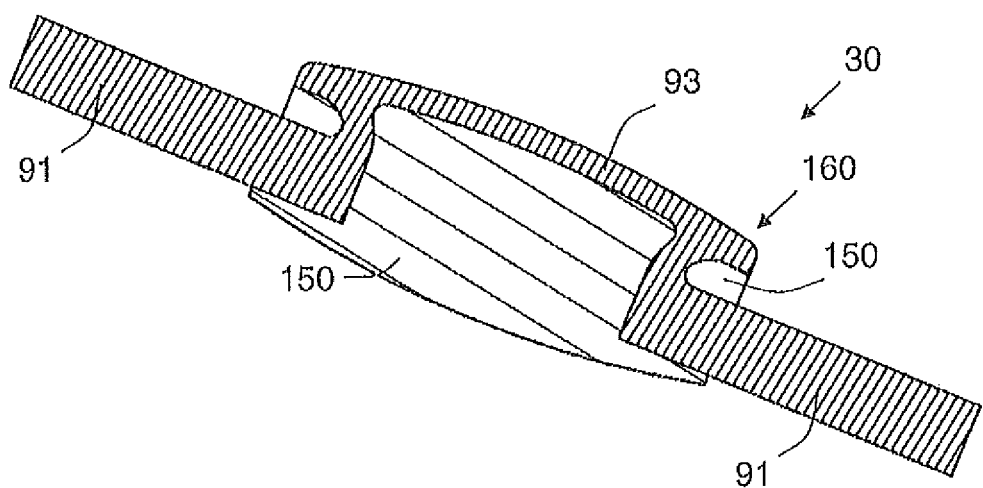
FIG. 8 is a section view B-B drawing of a haptic/optic assembly.
Figure 9:
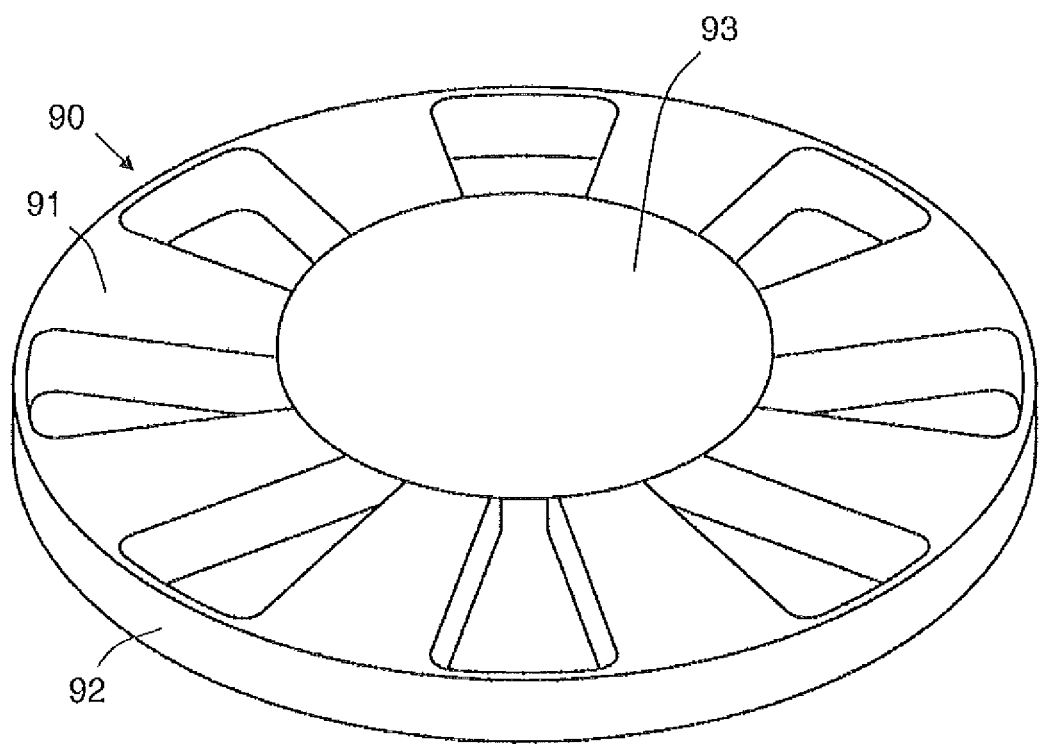
FIG. 9 is an anterior isometric drawing of the haptic of FIGS. 3-8.
Figure 10:
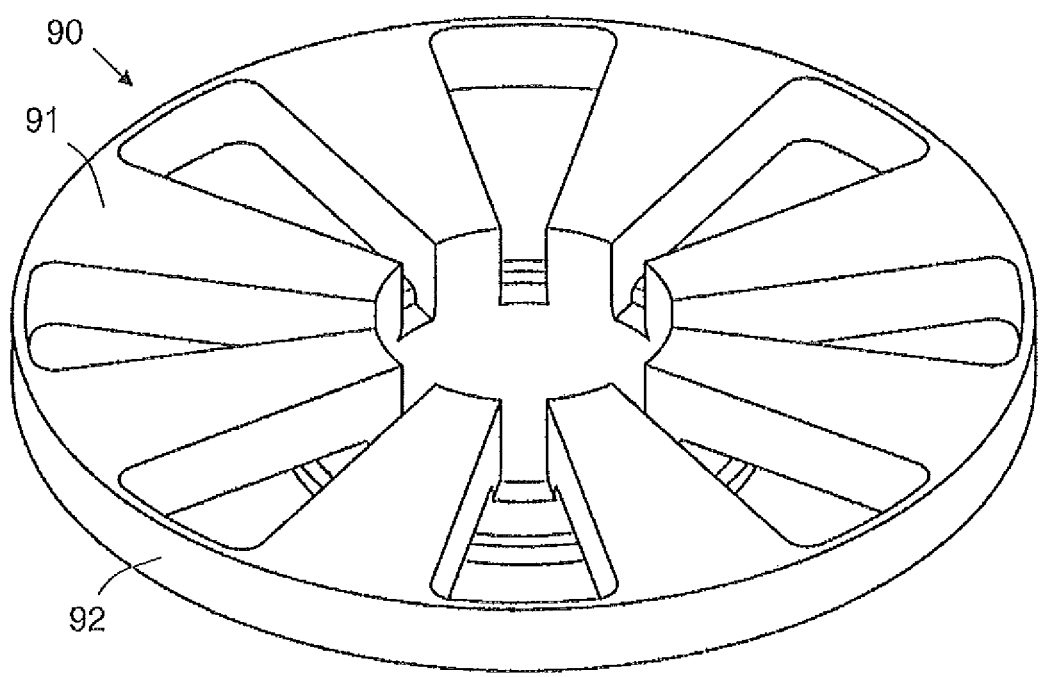
FIG. 10 is a posterior isometric drawing of the haptic of FIGS. 3-8.
Figure 11:
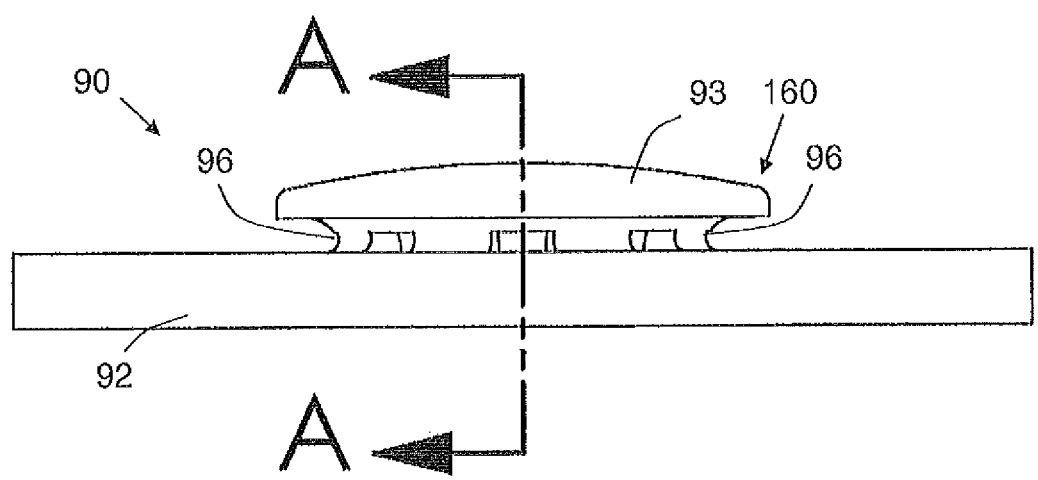
FIG. 11 is a front view drawing of the haptic of FIGS. 3-8.
Figure 12:
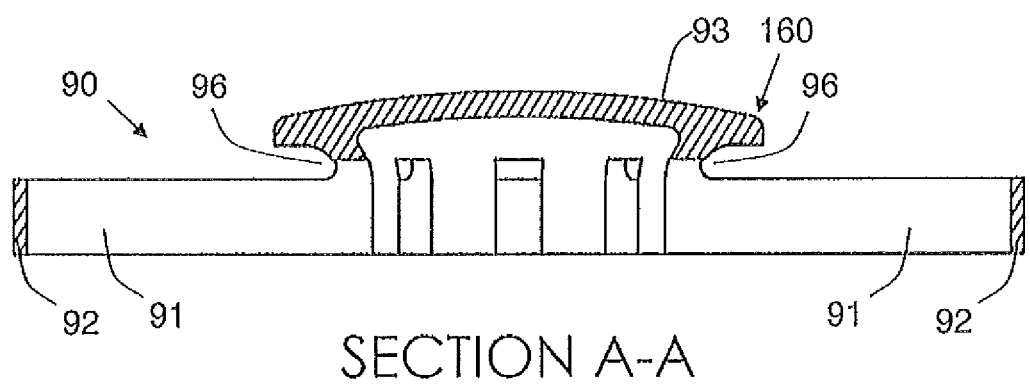
FIG. 12 is a section view A-A drawing of the haptic of FIGS. 3-8.
Figure 13:
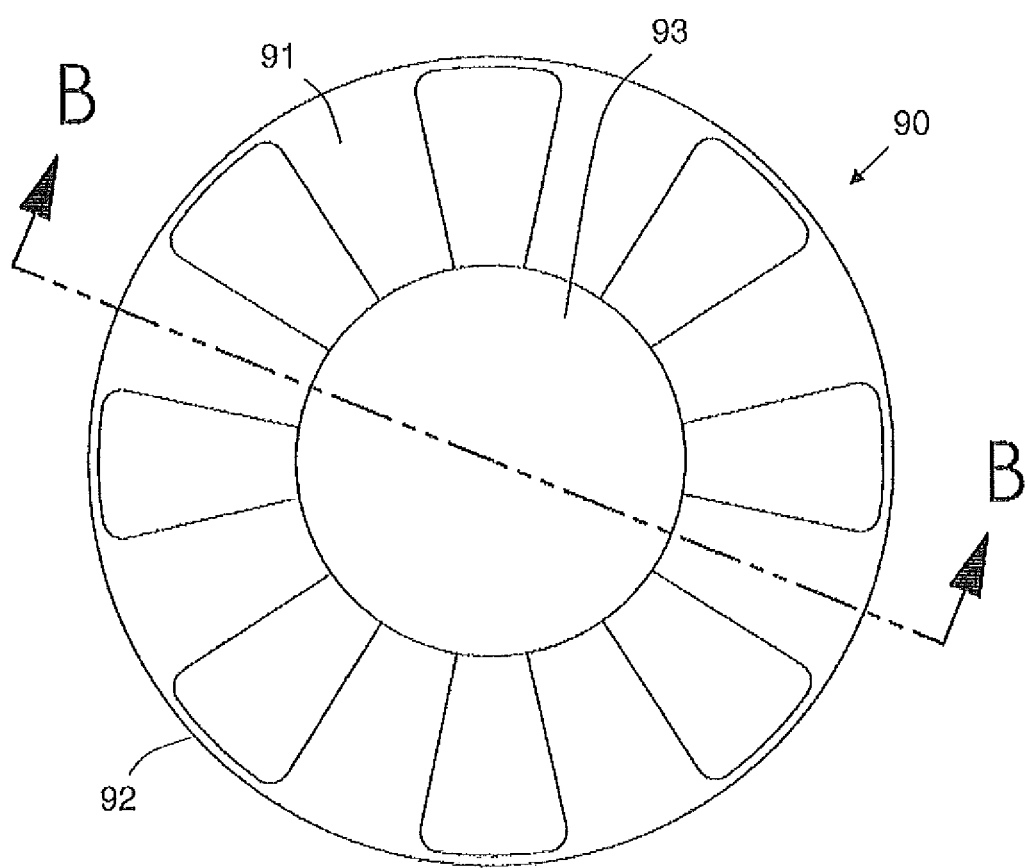
FIG. 13 is a top view drawing of the haptic of FIGS. 3-8.
Figure 14:
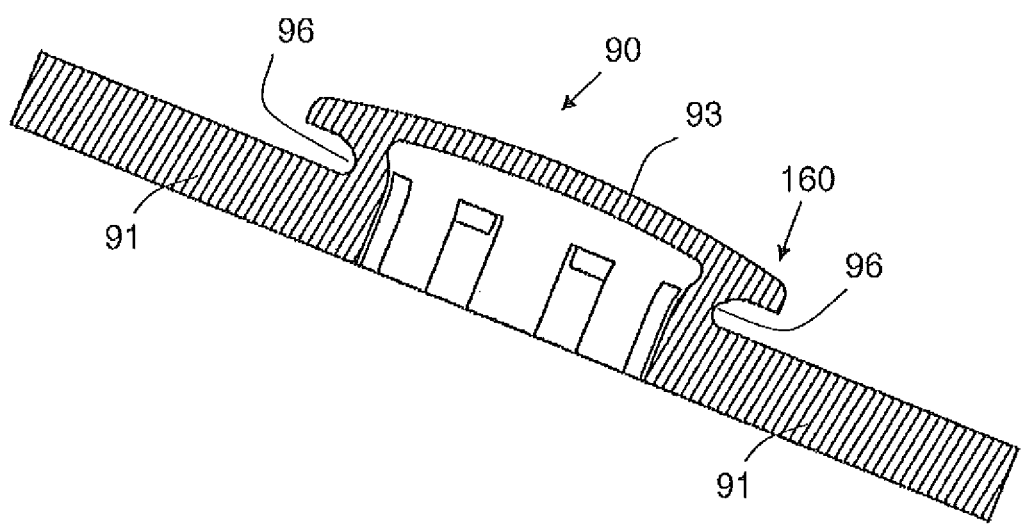
FIG. 14 is a section view B-B drawing of the haptic of FIGS. 3-8.
Figure 15:
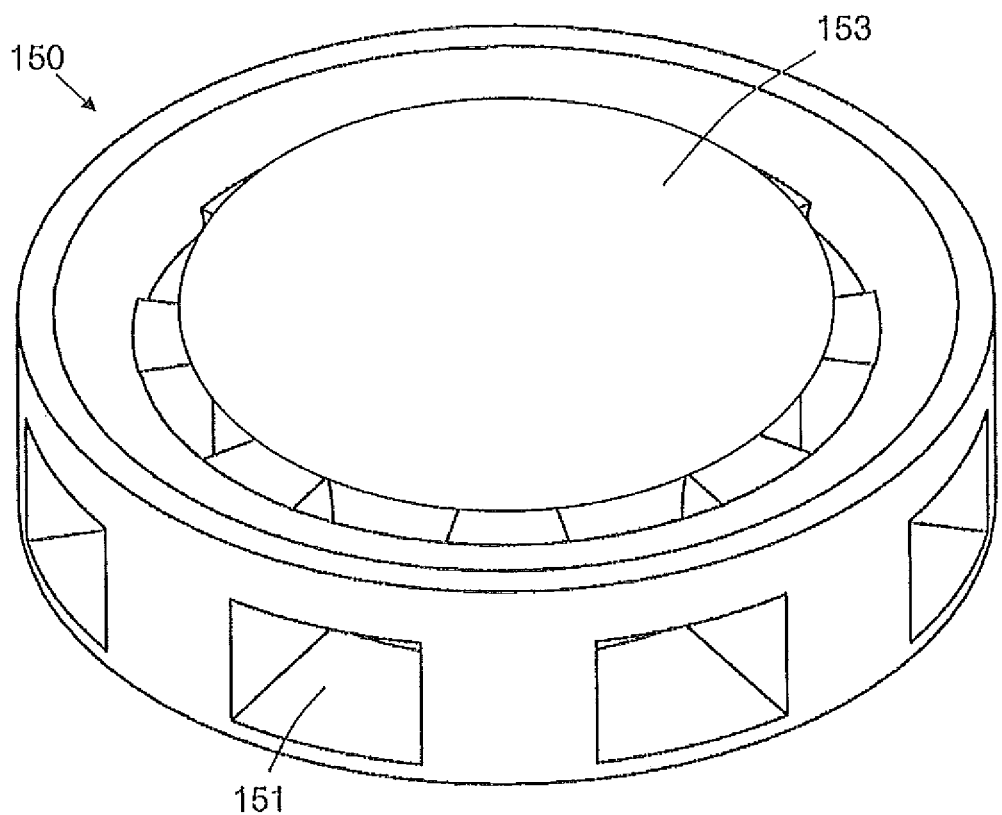
FIG. 15 is an anterior isometric drawing of the optic of FIGS. 3-8.
Figure 16:
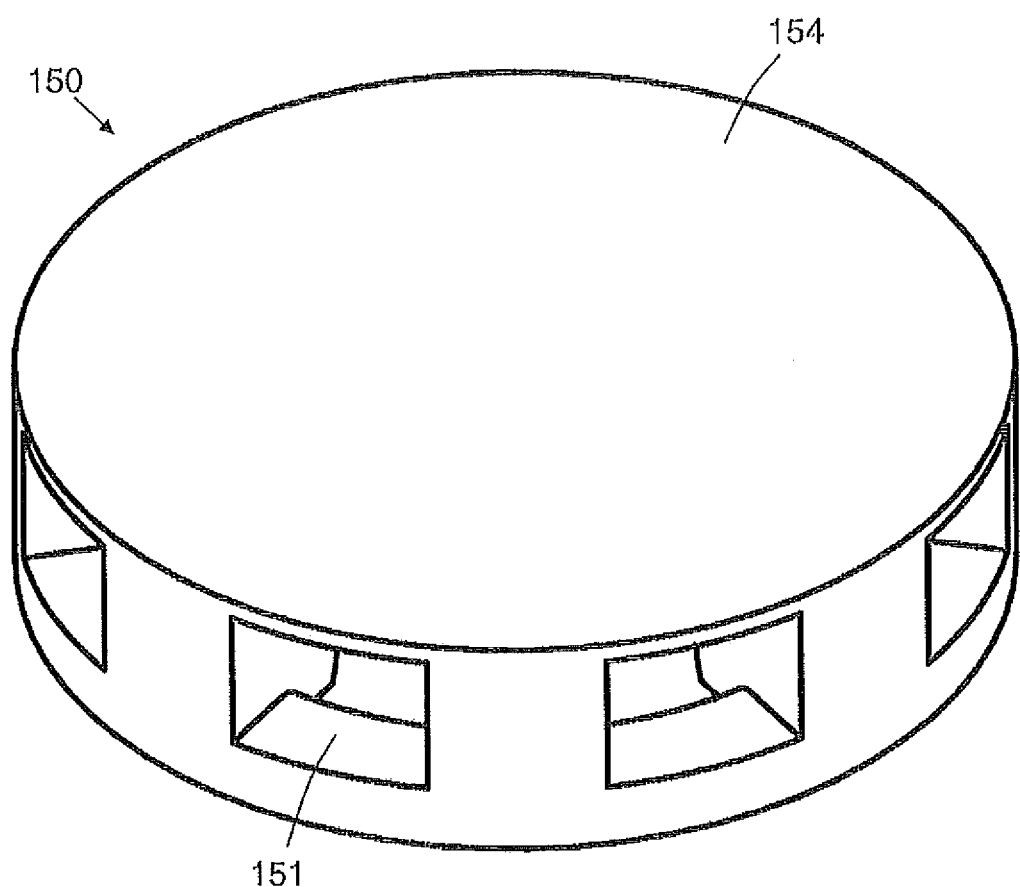
FIG. 16 is a posterior isometric drawing of the optic of FIGS. 3-8.
Figure 17:
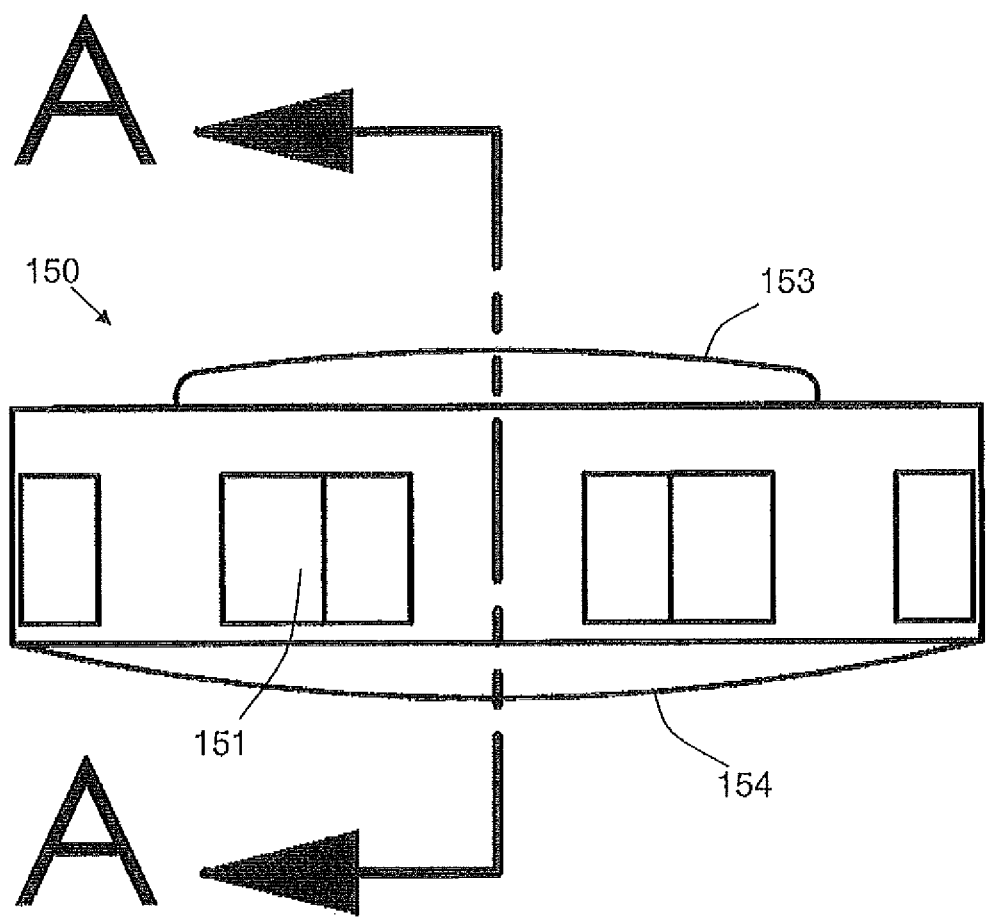
FIG. 17 is a front view drawing of the optic of FIGS. 3-8.
Figure 18:
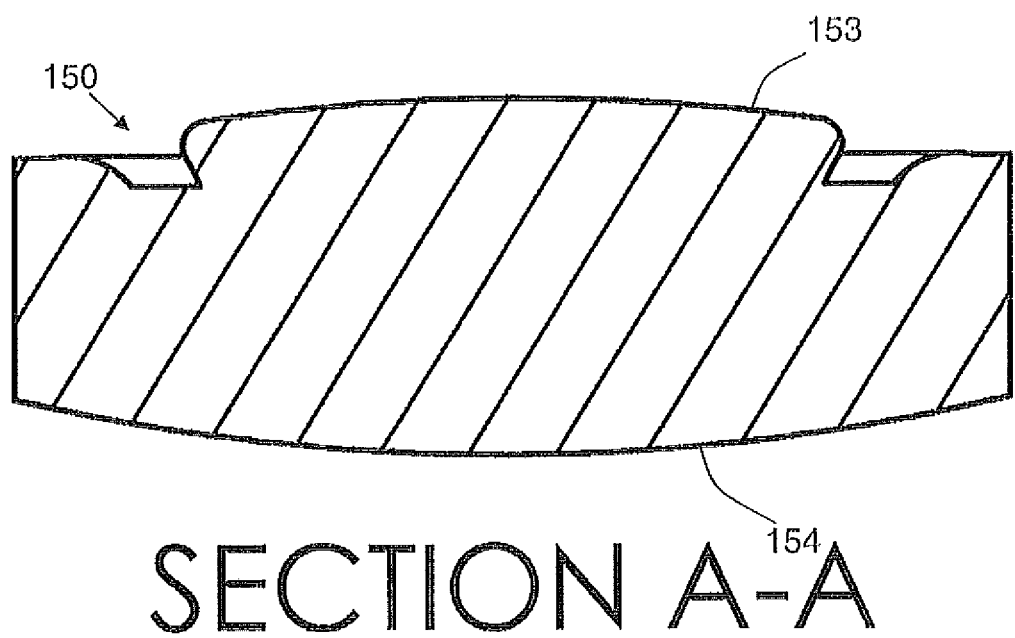
FIG. 18 is a section view A-A-drawing of the optic of FIGS. 3-8.
Figure 19:
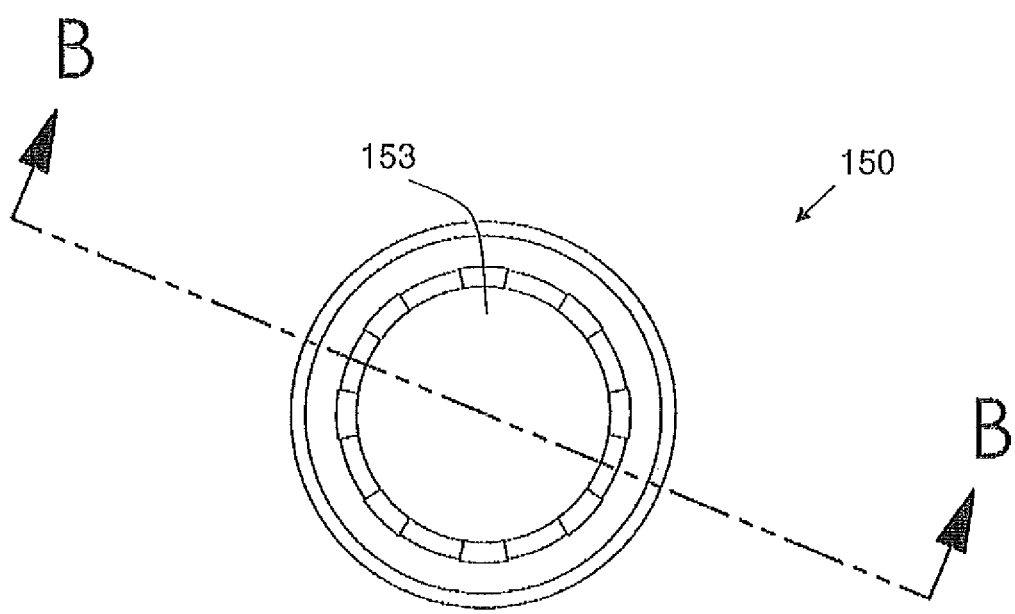
FIG. 19 is a top view drawing of the optic of FIGS. 3-8.
Figure 20:
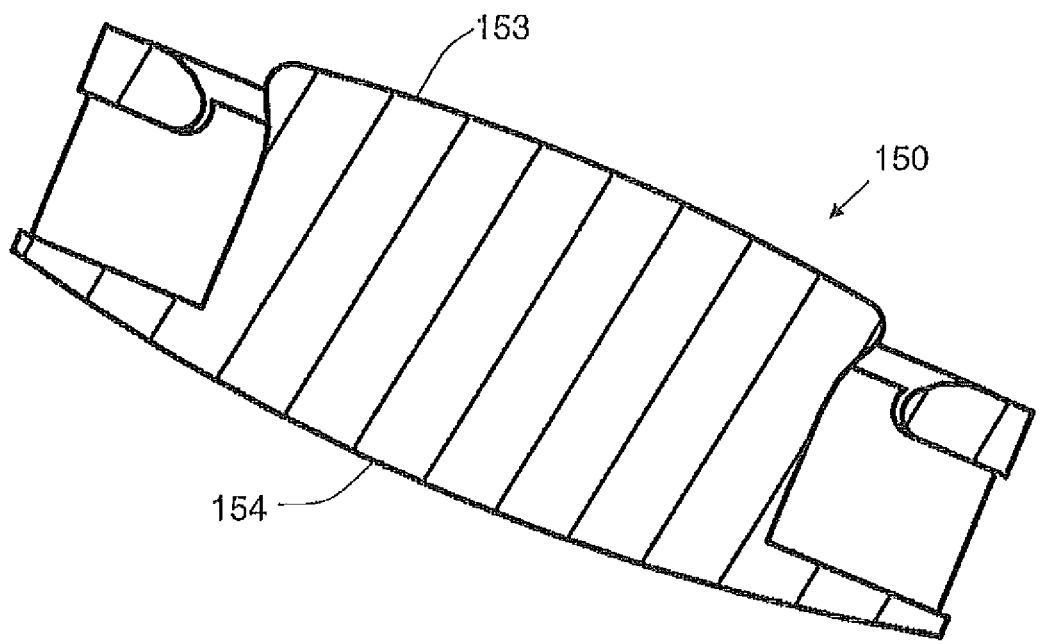
FIG. 20 is a section view B-B drawing of the optic of FIGS. 3-8.

From a top view, such as in FIG. 7, the haptic/optic assembly 30 appears similar to a wagon wheel, with individual haptic "spokes" or arms 91 radiating from a central optic cap towards a thin, continuous outer ring. From a cat-away side view, such as in FIG. 8, one sees that the central optic cap may be a thin, continuous membrane that balloons up from the haptic arms and forms a mushroom-like shape. The haptic 90 and optic 150 are described in greater detail below.

The haptic 90 may have various arms 91 or filaments extending radially from the outer edge 92 to the optic 150, located at or near the center of the lens. The haptic arms 91 may each be wedge-shaped, within the plane of the haptic 90, increasing in in-plane width from the inner portion to the outer edge of the haptic. Alternatively, the haptic arms 91 may have a constant in-plane width or an increasing in-plane width in all or portions, from the outer edge to the inner portion. The spaces between the haptic arms 91 may also be wedge-shaped, and may alternately include portions of constant in-plane width or increasing in-plane width, from the outer edge 92 to the inner portion.

The haptic arms 91 may be all connected at the outer edge 92 of the haptic 90. In some embodiments, the outer edge 92 may connect the arms 91 with a thin tangential portion having a radial thickness smaller than the tangential thickness of the haptic arms 91 themselves.

Figure 5:
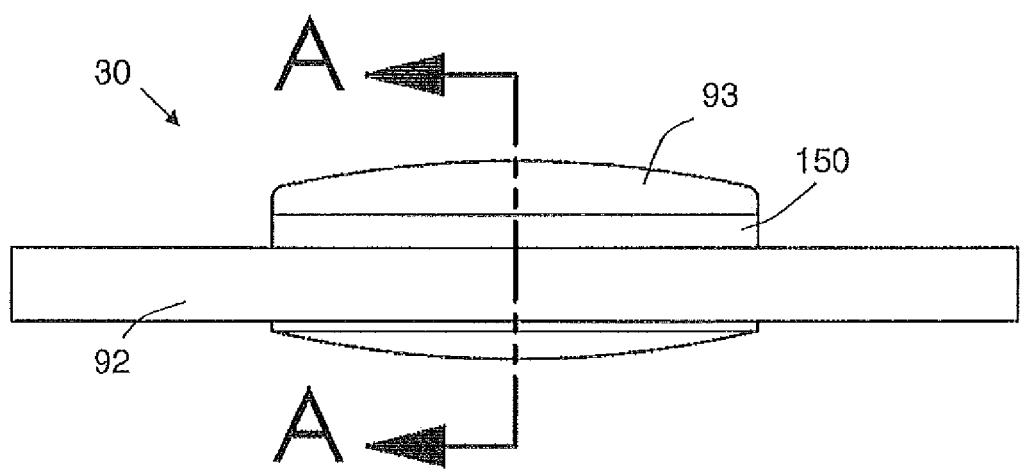
FIG. 5 is a front view-drawing of a haptic/optic assembly.
Figure 6:
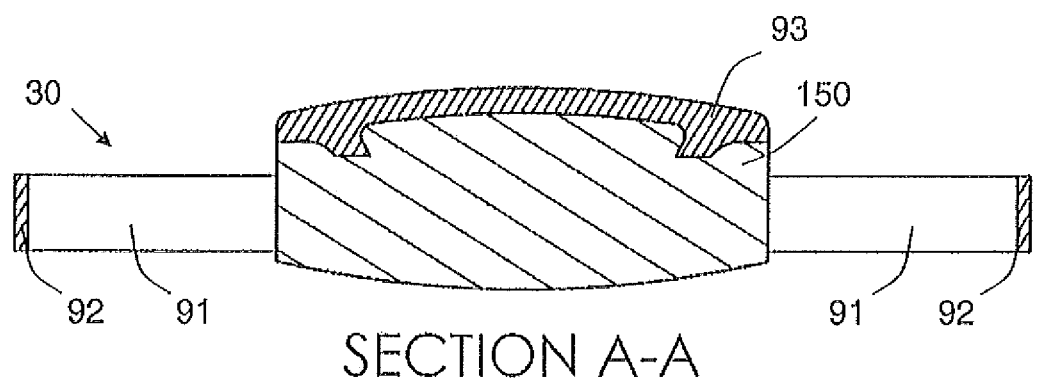
FIG. 6 is a section view A-A drawing of a haptic/optic assembly.

The haptic 90 itself may be essentially planar when seen from the side, as in FIG. 5, and may include generally flat and parallel anterior and posterior surfaces. Alternatively, the anterior and posterior surfaces of the haptic 90 may be tilted, inclined, or curved.

The intraocular lens further includes a cap 93 that extends over the anterior surface 153 of the optic 150. Alternatively, the cap 93 may extend over the posterior surface 154 of the lens. At the inner portion of the lens, the haptic arms 91 may connect to each other and/or to the cap 93. See, for instance, FIG. 8, which shows a cross-sectional view of the haptic 90 and the optic 150, and FIG. 14, which shows the same view but without the optic 150.

Note that the cap 93 may have a uniform thickness over its surface, or may optionally have a variable thickness over its surface. For instance, the cap 93 may be thicker in its center, near the optical axis of the lens, than at its periphery. Alternatively, the cap 93 may be thinner at its center than at its periphery. In general, the shape of the cap 93 over its surface helps determine the anterior and posterior surface shapes of the cap and the optic at each particular power within the accommodation range. In other words, the thickness May optionally vary over the surface of the cap, so that the capped surface shape deforms in a prescribed manner during accommodation. For instance, the cap 93 may include one or more aspheric and/or conic terms in its surface profile and/or its transmitted wavefront profile, which may help-reduce aberrations in the optical system of eye at one or more points within the range of accommodation.

In some embodiments, the cap is stiffer than the optic, so that if an anterior cap were not present, the curvature of the optic anterior surface would vary more during accommodation, compared to having the anterior cap present. This change in surface curvature. May be affected by the stiffness of the cap, so that a more stiff cap deforms less during accommodation than a less stiff cap, for comparable cap shapes. The surface deformation may also be affected by varying the thickness of the cap, so that a relatively thick cap may deform less than a relatively thin cap, for comparable material moduli.

In some embodiments, the presence of a cap on the anterior face of the lens may help ensure that the lens vaults in the anterior direction during accommodation. More specifically, if a lens having an anterior cap is squeezed radially around its equator by the capsular bag, the cap may help ensure that at least one of the lens surfaces translates away from the retina.

Note that near the innermost portion of the lens, each haptic arm 91 includes an out-of-plane curved portion 96, in which the haptic arm 91 protrudes out of the plane of the haptic 90 and attaches to the cap 93. This haptic detail is seen most clearly in the haptic-only pictures in FIGS. 9-14.

The out-of-plane curved portion 96 may be considered to be part of a so-called "coupling member" or "force transfer member" 160, which mechanically couples the generally planar structure of the haptic 90 to the cap 93. As the capsular bag changes shape and/or size, the haptic arms 91 compress or expand radially, and the force transfer member 160 couples this radial compression or expansion to the cap 93. It may be helpful to think of the force transfer member 160 as being analogous to a hinge, with a bending occurring at the out-of-plane curved portion 96. The force transfer member 160 may optionally include a portion around the circumference of the cap, which extends radially beyond the out-of-plane curved portion 96. In general, the shape and features of the force transfer member 160 helps determine the anterior and posterity surface shapes of the cap and the optic at each particular power within the accommodation range.

Note that when the optic 150 is present, the optic 150 obscures much of the inner detail of the haptic 90, as seen from FIGS. 3-5 and 7. This is most easily understood from an explanation of an exemplary manufacturing process for the lens. First, the haptic is produced by a molding process. Next, the optic is inserted onto/into the haptic by a second molding process, in which the softer optic material fills the cap 93 and encapsulates a portion of the haptic arms. The optic extends posteriorly out of the general plane of the haptic arms, and forms an essentially continuous posterior surface 154 to the optic 150. When viewed from the edge, as in FIG. 5, the assembled haptic/optic assembly therefore has a cap 93 made from the haptic material, and an optic 150 that extends from the cap 93 through the plane of the haptic 90 to the posterior surface 154 of the optic 150. The anterior surface 153 of the optic 150 is hidden in this assembled view, and is generally flush with the cap 93 of the haptic 90. The optic 150, when viewed separately from the haptic 90, may include various holes 151 that accommodate the haptic arms 91, and several other features on or near its anterior side, ultimately it is easiest to describe the shape of the optic as filling in a central portion of the lens and occupying a particular volume that is not occupied by the haptic itself.

The optic 150 and the haptic 90 may generally be constructed of any of the various types of material known in the art. For example, the optic 150 and/or the haptic 90 may be of a resiliently deformable or foldable material such as silicone polymeric materials, acrylic polymeric materials, hydrogel-forming polymeric materials (e.g., polyhydroxyethylmethacrylate, polyphosphazenes, polyurethanes, and mixtures thereof), and the like. Other advanced formulations of silicone, acrylic, or mixtures thereof are also anticipated. Selection parameters for suitable lens materials are well known to those of skill in the art. See, for example, David J. Apple, et al., Intraocular Lenses: Evolution, Design, Complications, and Pathology, (1989) William & Wilkins, which is herein incorporated by reference. The optic and/or haptic materials may be selected to have a relatively high refractive index, and thus provide a relatively thin optic, for example, having a center thickness in the range of about 150 microns to about 1000 microns, depending on the material and the optical power of the lens.

The haptic 90 and/or the cap 93 may be generally stiffer than the optic. In some embodiments, the haptic 90 and/or the cap 93 are made stiffer by selecting a material with a higher modulus than that of the optic 150 material. For instance, the haptic/cap material may have a typical modulus of elasticity in the range of 500-1500 kPa or greater, while a typical optic material may have a modulus that is less than 500 kPa, less than 100 kPa, or within the range of 25 kPa to 50 kPa. The haptic material and optic material may both be transparent, so that light may transmit through the cap 93 of the haptic 90, and so that the haptic arms 91 may occupy a portion of the pupil of the lens without obstructing any light.

It may be preferable to have the refractive index of the haptic 90 material be matched to that of the optic 150 material, which may reduce or minimize any reflections that arise at the interfaces between the haptic 90 and optic 150. Alternatively, the refractive indices of the haptic material may be selected to be different from that of the optic material. Additionally or alternatively, the dispersion of the haptic and optic materials may be selected to be different, for example, to provide at least some chromatic correction to light entering the eye of a subject into which the optic 150 is placed. A typical range for these refractive indices is about 1.43 to about 1.56, although any suitable range may be used. In general, the haptic and the optic may be considered to be "refractive index-matched" if their refractive indices are equal for at least one wavelength that lies within the visible spectrum, or between 400 nm and 700 nm. A typical center thickness for the optic is in the range of about 2.0-2.5 mm. A typical edge thickness for the optic is in the range of about 1.0-1.5 mm.

There are several advantages to the exemplary haptic/optic assembly 30 shown in FIGS. 3-20, compared to known accommodating intraocular lenses that lack a cap 93.

A first advantage is that during accommodation, the axial movement of the lens may be biased anteriorly. In its relaxed state, in which the eye is focused on a distant object, the zonular fibers and the capsular bag of the eye are expanded radially around the equator of the intraocular lens, and the haptic remains largely in a single plane, as in FIG. 5. In its accommodative state, in which the eye is focused on a relatively close object, the zonular fibers and the capsular bag of the eye are compressed radially around the equator of the intraocular lens. The haptic develops a cone-like shape, in which its equator remains coincident with the capsular bag and its central portion is bowed out in the anterior direction. In this bowed-out state, the optic may translated away from its "relaxed" position, with the translation occurring in the anterior direction. In other words, when the eye focuses on a close object, the optic may be translated away from the retina. This anterior translation during accommodation assists the optic in focusing a "near" image on the retina, and eases the forces required from the zonular fibers for a particular accommodation range. In contrast, a posterior translation would work against the optic, and would require a significantly larger force exerted by the zonular fibers on the capsular bag for a similar accommodation range.

A second advantage is that the anterior cap may protect the relatively soft optic material. The anterior cap may be made from the haptic material, which may be significantly stiffer or harder than the optic material. As a result, the relatively soft anterior surface of the optic may be protected by the anterior cap, and may be less susceptible to damage such as scratching during installation. In addition, because the optic material may be relatively tacky or sticky, the layer of haptic material in the anterior cap may improve the ability to handle the lens by reducing the area of exposed tacky optic material.

A third advantage is that the power change of the lens arises primarily from the deformation of the anterior surface of the optic, while the posterior surface does not include a power change that significantly offsets that from the anterior surface. In other words, the posterior surface may deform slightly during accommodation, but the power change of the posterior surface may be relatively small and/or may aid in accommodation. In contrast, if the power change of the posterior were to partially offset the increase in power of the full lens for accommodation, then a larger force would be required of the zonular fibers and capsular bag in the eye, for a particular range of accommodation.

In one embodiment, the lens may include a posterior cap of haptic material over the posterior surface of the lens. This optional posterior cap may protect the posterior surface of the optic, and may ease the handling requirements of the optic before and during installation. This posterior cap may be thinner than the anterior cap, or may alternatively be the same thickness or thicker than the anterior cap. The thickness may optionally vary over the surface of the posterior cap. The posterior cap may be made of the same material as the anterior cap, or may be may from a different material. The stiffnesses of the anterior and posterior cap may be the same, or may be different.

In one embodiment, the lens may include a posterior cap but no anterior cap.

In one embodiment, the anterior cap may be made from multiple layers, in which one layer may be made from the haptic material, and the other layer or layers may be made from a different material having the same stiffness or a different stiffness.

In one embodiment, the thickness of the anterior cap may vary across the anterior surface. For instance, the center of the cap may be thicker than the edges of the cap. Alternatively, the anterior cap may be essentially uniform over the anterior surface of the optic.

The description of the invention and its applications as set forth herein is illustrative and is not intended to limit the scope of the invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

What is claimed is:

1. An intraocular lens cap assembly, comprising:
   a cap for positioning adjacent to and on at least one of an anterior and posterior face of an adjustable optic of an intraocular lens;
   a haptic having a surface defining a plane extending between the haptic and the cap;
   the haptic including arms operably coupled to the cap, at least a portion of the arms extending radially within the optic, and the haptic further includes a force transfer member that extends radially inward towards the cap, the force transfer member having an out-of-plane portion extending from the arm towards the cap and through the plane of the haptic, and the optic extending through the force transfer member, the force transfer member configured to change the curvature of the cap in response to a force resulting in an accommodated state;
   wherein the cap has an inner surface facing at least one of the anterior or posterior face of the adjustable optic, and the inner surface is configured to remain in direct contact with at least one of the anterior or posterior face of the adjustable optic in the accommodated state.

2. The intraocular lens cap assembly of claim 1, further comprising a secondary cap;
   wherein the cap is adjacent to one of the anterior face and the posterior face of the adjustable optic, and the secondary cap is adjacent to and on the other of the anterior face and the posterior face of the adjustable optic.

3. The intraocular lens cap assembly of claim 2, wherein the cap and the secondary cap are made from materials having different stiffnesses.

4. The intraocular lens cap assembly of claim 1, wherein the force is an ocular force.

5. The intraocular lens cap assembly of claim 1, wherein the force transfer member includes a hinge.

6. The intraocular lens cap assembly of claim 1 further comprising one or more aspheric and/or conic terms in its surface profile.

7. The intraocular lens cap assembly of claim 1, wherein the cap has a uniform thickness.

8. The intraocular lens cap assembly of claim 1, wherein the cap has a variable thickness.

9. The intraocular lens cap assembly of claim 1, wherein the force transfer member includes a portion extending around the circumference of the cap such that the arms extend radially between the portion and the optic.

10. The intraocular lens cap assembly of claim 9, wherein the out-of-plane curved portion is located a distal end of the arm, opposite the portion.

11. The intraocular lens cap assembly of claim 1, wherein the force transfer member is located within a through hole of the optic.

* * * * *